(12) United States Patent
Feng et al.

(10) Patent No.: US 9,872,828 B2
(45) Date of Patent: Jan. 23, 2018

(54) EMULSION OF CROSS-LINKED AMINOSILOXANE POLYMER

(71) Applicant: Dow Corning Corporation, Midland, MI (US)

(72) Inventors: Qian J. Feng, Midland, MI (US); Bethany K. Johnson, Midland, MI (US); Zhi Li, Midland, MI (US); Donald T. Liles, Midland, MI (US); Kimmai Nguyen, Midland, MI (US); Timothy Andrew Roggow, II, Chesaning, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 15/125,800

(22) PCT Filed: Mar. 16, 2015

(86) PCT No.: PCT/US2015/020640
§ 371 (c)(1),
(2) Date: Sep. 13, 2016

(87) PCT Pub. No.: WO2015/179011
PCT Pub. Date: Nov. 26, 2015

(65) Prior Publication Data
US 2017/0000722 A1   Jan. 5, 2017

Related U.S. Application Data

(60) Provisional application No. 62/001,415, filed on May 21, 2014.

(51) Int. Cl.
| | | |
|---|---|---|
| *A61K 8/898* | (2006.01) | |
| *A61Q 5/06* | (2006.01) | |
| *A61K 8/06* | (2006.01) | |
| *A61K 8/891* | (2006.01) | |

(52) U.S. Cl.
CPC ............. *A61K 8/898* (2013.01); *A61K 8/06* (2013.01); *A61K 8/891* (2013.01); *A61Q 5/06* (2013.01)

(58) Field of Classification Search
CPC ........ A61K 8/06; C07K 14/265; C08G 77/26; C08G 77/388
See application file for complete search history.

(56) References Cited

U.S. PATENT DOCUMENTS

| | | | |
|---|---|---|---|
| 2,798,053 A | 7/1957 | Brown | |
| 3,597,268 A | 8/1971 | Smith | |
| 3,953,581 A | 4/1976 | Ehlers et al. | |
| 3,962,418 A | 6/1976 | Birkofer | |
| 4,009,256 A | 2/1977 | Nowak, Jr. et al. | |
| 4,070,152 A | 1/1978 | Pentz | |
| 4,290,974 A | 9/1981 | Bouillon et al. | |
| 4,304,730 A | 12/1981 | Bouillon et al. | |
| 4,311,626 A | 1/1982 | Ona et al. | |
| 4,323,549 A | 4/1982 | Bouillon et al. | |
| 4,327,031 A | 4/1982 | Bouillon et al. | |
| 4,330,488 A | 5/1982 | Bouillon et al. | |
| 4,387,089 A | 6/1983 | De Polo | |
| 4,406,880 A | 9/1983 | Bouillon et al. | |
| 4,489,057 A | 12/1984 | Welters et al. | |
| 4,562,067 A | 12/1985 | Hopp et al. | |
| 4,585,597 A | 4/1986 | Lang et al. | |
| 4,704,272 A | 11/1987 | Oh et al. | |
| 4,775,526 A | 10/1988 | Lang et al. | |
| 4,788,006 A | 11/1988 | Bolich, Jr. et al. | |
| 5,391,400 A | 2/1995 | Yang | |
| 5,399,652 A | 3/1995 | Bindl et al. | |
| 5,643,557 A | 7/1997 | Eteve et al. | |
| 5,690,915 A | 11/1997 | Eteve et al. | |
| 5,690,917 A | 11/1997 | Eteve et al. | |

(Continued)

FOREIGN PATENT DOCUMENTS

| | | |
|---|---|---|
| AU | 199052435 | 10/1990 |
| EP | 0487404 | 11/1991 |
| FR | 2282426 | 2/1974 |
| WO | 1995022331 | 8/1995 |
| WO | 2003101412 | 12/2003 |
| WO | 2003105789 | 12/2003 |
| WO | 2003105801 | 12/2003 |
| WO | 2003106614 | 12/2003 |
| WO | 2004000247 | 12/2003 |
| WO | 2004054523 | 7/2004 |
| WO | 2004054524 | 7/2004 |
| WO | 2004060101 | 7/2004 |
| WO | 2004060271 | 7/2004 |
| WO | 2004060276 | 7/2004 |
| WO | 2015179513 | 11/2015 |

OTHER PUBLICATIONS

Bibliographic data: FR2282426 (A2)—Mar. 19, 1976.

*Primary Examiner* — Anna R Falkowitz
(74) *Attorney, Agent, or Firm* — Timothy J. Troy

(57) ABSTRACT

An emulsion includes a liquid continuous phase and a dispersed phase including a cross-linked aminosiloxane polymer. The cross-linked aminosiloxane polymer includes a first siloxane backbone, a second siloxane backbone, and at least one intramolecular structure cross-linking a silicon atom of the first siloxane backbone and a silicon atom of the second siloxane backbone. The intramolecular structure has the chemical structure: (Formula (I)) wherein X is chosen from the following groups; (Formula (II)); (Formula (III)); or (Formula (IV)) wherein each R is independently a $C_{-1}$-$C_{-10}$ hydrocarbon group, each $R^1$ is independently a $C_{-1}$-$C_{-10}$ hydrocarbon group, each $R^2$ is independently a hydrogen atom, OH, a $C_{-1}$-$C_{-12}$ hydrocarbon group, a phenyl group, R'(OR")$_m$ wherein m is 1 to 3, or R'OH, wherein each of R' and R" is independently an alkyl group, and wherein a is 0 or 1. This disclosure also provides a method of forming the emulsion.

20 Claims, 1 Drawing Sheet

(56) References Cited

U.S. PATENT DOCUMENTS

| | | |
|---|---|---|
| 5,695,747 A | 12/1997 | Forestier et al. |
| 5,708,070 A | 1/1998 | Joffre et al. |
| 5,788,955 A | 8/1998 | Eteve et al. |
| 5,795,565 A | 8/1998 | Eteve et al. |
| 5,919,441 A | 7/1999 | Mendolia et al. |
| 5,981,680 A | 11/1999 | Petroff et al. |
| 6,051,216 A | 4/2000 | Barr et al. |
| 6,248,855 B1 | 6/2001 | Dalle et al. |
| 6,329,462 B1 | 12/2001 | Hale et al. |
| RE38,116 E | 5/2003 | Petroff et al. |
| 7,078,026 B2 | 7/2006 | Ferrari et al. |
| 8,455,603 B2 | 6/2013 | Ferenz et al. |
| 2003/0068348 A1 | 4/2003 | Ferrari et al. |
| 2003/0072730 A1 | 4/2003 | Tournilhac |
| 2003/0170188 A1 | 9/2003 | Ferrari et al. |
| 2003/0235553 A1 | 12/2003 | Lu et al. |
| 2004/0180032 A1 | 9/2004 | Manelski et al. |
| 2006/0269506 A1 | 11/2006 | De Caire et al. |
| 2008/0254076 A1 | 10/2008 | Ferrari et al. |
| 2011/0039087 A1 | 2/2011 | Cauvin et al. |
| 2011/0230633 A1 | 9/2011 | Ferenz et al. |
| 2012/0149930 A1* | 6/2012 | Moriya ............ A61K 8/898 556/419 |

* cited by examiner

EMULSION OF CROSS-LINKED AMINOSILOXANE POLYMER

CROSS REFERENCE TO RELATED APPLICATIONS

This application is a U.S. national stage filing under 35 U.S.C. § 371 of PCT Application No. PCT/US15/020640 filed on 16 Mar. 2015, currently pending, which claims the benefit of U.S. Provisional Patent Application No. 62/001,415 as filed on May 21, 2014, under 35 U.S.C. § 119 (e). PCT Application No. PCT/US15/020640 and U.S. Provisional Patent Application No. 62/001,415 are hereby incorporated by reference.

FIELD OF THE DISCLOSURE

This disclosure generally relates to an emulsion including a liquid continuous phase and a dispersed phase including a cross-linked aminosiloxane polymer that includes an intramolecular structure having a particular chemical formula.

BACKGROUND

The desire to have hair retain a particular shape is widely held. The two methodologies of accomplishing this are permanent chemical alteration of the hair or temporary alteration. A temporary alteration is one which can be removed by water or by shampooing. This has generally been accomplished by means of applying a composition to dampened hair after shampooing and/or conditioning and prior to drying and/or styling. The materials used to provide setting benefits are resins or gums and are sold in the form of mousses, gels, lotions, or sprays. However, these materials tend to increase difficulty with combing the hair, degrade hair feel, and can be difficult to work with. Accordingly, there remains an opportunity for improvement.

SUMMARY OF THE DISCLOSURE

This disclosure provides an emulsion including a liquid continuous phase and a dispersed phase including a cross-linked aminosiloxane polymer. The cross-linked aminosiloxane polymer includes a first siloxane backbone, a second siloxane backbone, and at least one intramolecular structure cross-linking a silicon atom of the first siloxane backbone and a silicon atom of the second siloxane backbone. The intramolecular structure has the chemical structure:

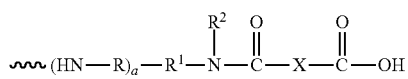
(I)

wherein X is chosen from the following groups;

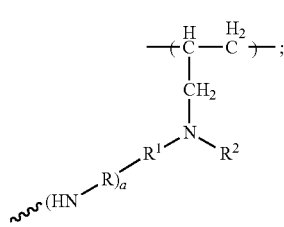
(II)

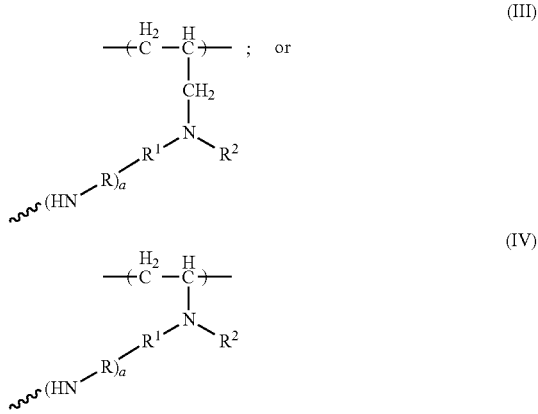

wherein each R is independently a $C_1$-$C_{10}$ hydrocarbon group, each $R^1$ is independently a $C_1$-$C_{10}$ hydrocarbon group, each $R^2$ is independently a hydrogen atom, OH, a $C_1$-$C_{12}$ hydrocarbon group, a phenyl group, $R'(OR'')_m$ wherein m is 1 to 3, or R'OH, wherein each of R' and R'' is independently an alkyl group, and wherein a is 0 or 1. This disclosure also provides a method of forming the emulsion.

BRIEF DESCRIPTION OF THE DRAWING

Other advantages of the present disclosure will be readily appreciated, as the same becomes better understood by reference to the following detailed description when considered in connection with the accompanying drawings.

DETAILED DESCRIPTION OF THE DISCLOSURE

Figure 1:
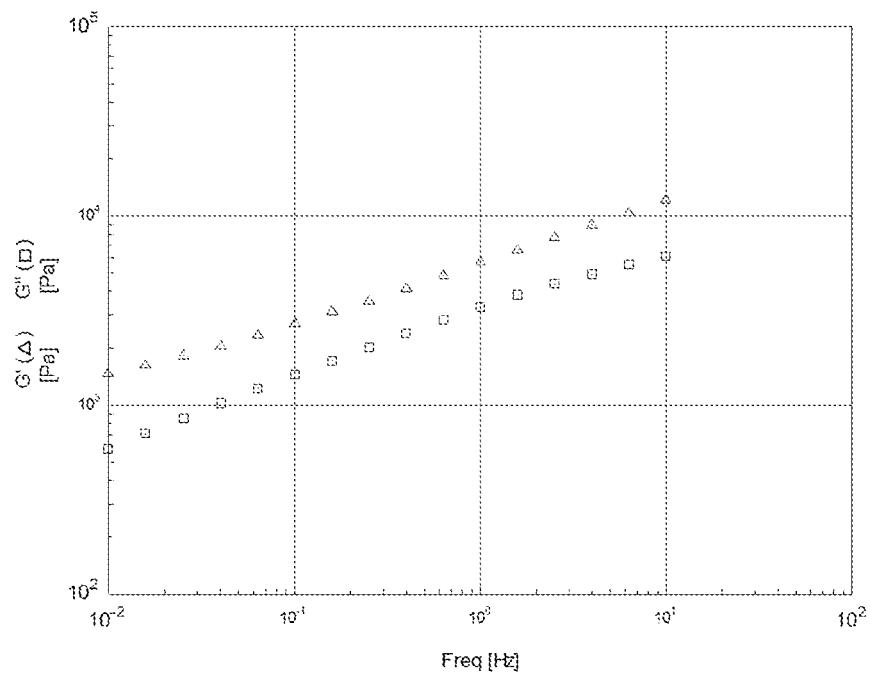
FIG. 1 is a plot of frequency modulation as related to Example 1.

This disclosure provides an emulsion. The emulsion typically includes a liquid continuous phase and a dispersed phase that is dispersed in the continuous phase. The dispersed phase may be liquid, solid, gel, elastomer, rubber, etc. Alternatively, the emulsion may include a liquid continuous phase and a solid, gel, elastomer, or rubber dispersed phase and be more accurately described as a dispersion. However, for purposes of this disclosure, the terminology "dispersion" and "emulsion" are used interchangeably.

The dispersed phase of the emulsion typically includes or is particles of a cross-linked aminosiloxane polymer, described in greater detail below and hereinafter described as the "aminosiloxane polymer."

The aminosiloxane polymer may be present in the emulsion in an amount of from 0.1 to 90, 10 to 70, or 15 to 60, parts by weight per 100 parts by weight of the emulsion. In other embodiments, the aminosiloxane polymer is present in an amount of from 5 to 90, 10 to 85, 15 to 80, 20 to 75, 25 to 70, 30 to 65, 35 to 60, 40 to 55, or 45 to 50, parts by weight per 100 parts by weight of the emulsion. All values and ranges of values therebetween the aforementioned values are hereby expressly contemplated in various non-limiting embodiments.

The terminology "particle" may refer to a single particle or a plurality of particles. Thus, the terminology "particle" and "particles" are used interchangeably herein. Typically, the particles are dispersed in the emulsion. In other words, the particles may be "dispersed particles." The particles themselves may be solids, gels, liquids, or combinations thereof. The particles are usually liquids or solids that are immiscible with, and dispersed in, a liquid continuous phase. The particles may include liquids as diluents, such that no external or additional liquids are added to the emulsion. Alternatively, the emulsion may include a liquid independent of any diluent.

The particles may be of varying sizes. In various embodiments, the emulsion includes particles having a size, e.g. by volume, from 1 nm to 10 µm, of less than 1 µm, from 1 nm to 1 µm, of from 100 nm to 1000 nm, from 10 nm to 200 nm or from 0.2 to 5 microns. In other embodiments, the emulsion includes particles having a size, e.g. by volume, from 20 to 190, from 30 to 180, from 40 to 170, from 50 to 160, from 60 to 150, from 70 to 140, from 80 to 130, from 90 to 120, or from 100 to 110 nm. In still other embodiments, the emulsion includes particles having a size, e.g. by volume, of from 0.3 to 4.9, from 0.4 to 4.8, from 0.5 to 4.7, from 0.6 to 4.6, from 0.7 to 4.5, from 0.8 to 4.4, from 0.9 to 4.3, from 1 to 4.2, from 1.1 to 4.1, from 1.2 to 4, from 1.3 to 3.9, from 1.4 to 3.8, from 1.5 to 3.7, from 1.6 to 3.6, from 1.7 to 3.5, from 1.8 to 3.4, from 1.9 to 3.3, from 2 to 3.2, from 2.1 to 3.1, from 2.2 to 3, from 2.3 to 2.9, from 2.4 to 2.8, from 2.5 to 2.7, or from 2.5 to 2.6, microns. All values and ranges of values therebetween the aforementioned values are hereby expressly contemplated in various non-limiting embodiments.

In another embodiment, the emulsion may be classified as a nanoemulsion. The emulsion may include particles smaller or larger than the sizes described immediately above, depending on the desire of those of skill in the art. The particles typically have a dynamic viscosity of from 10 to 1E7 or 1E3 to 1E6, cP, measured using a rheometer with an oscillation procedure (frequency sweep) of from $10^2$ to $10^{-3}$ Hz. However, the particles can have a dynamic viscosity outside of this range if desired. All values and ranges of values therebetween the aforementioned values are hereby expressly contemplated in various non-limiting embodiments.

In one embodiment, the emulsion includes a liquid (as the continuous phase) and the particles are dispersed in the liquid. Alternatively, the liquid may be an external liquid that is added independently of any other component. In one embodiment, the liquid is a non-polar liquid. In another embodiment, the liquid is a polar liquid such as an alcohol or water. Typically, the liquid is water. The water may be tap water, well water, purified water, deionized water, and combinations thereof and may be present in the emulsion in varying amounts depending on the type of emulsion. In another embodiment, the emulsion includes a non-polar liquid (e.g., non-polar liquid particles) as the dispersed phase and a polar liquid as the continuous phase. In various embodiments, the liquid may be present in amounts of from 20 to 80, of from 30 to 70, of from 40 to 60, or in an amount of about 50, parts by weight per 100 parts by weight of the emulsion, so long as a total amount of the emulsion does not exceed 100 parts by weight.

The emulsion may be further defined as a "colloid" or "colloid dispersion," terminology which can be used interchangeably. Typically, colloids include particles of less than 100 nanometers in size dispersed in the continuous phase. Colloids may be classified in numerous ways. The colloid may be reversible (i.e., exist in more than one state) or irreversible. Further, the colloid may be elastomeric or viscoelastic.

As is understood in the art, emulsions are typically classified into one of four categories according to a chemical nature of the dispersed and continuous phases. A first category is an oil-in-water (O/W) emulsion. O/W emulsions typically include a non-polar dispersed phase (e.g., oil) in an aqueous continuous phase (e.g. water) which forms particles. For purposes of the instant disclosure, the terminology "oil" includes non-polar molecules, may include any non-polar compound, and may include the particles of the disclosure. A second category of emulsion is a water-in-oil (W/O) emulsion. W/O emulsions typically include a polar dispersed phase such as water or other hydrophilic substances or mixtures thereof in a non-polar continuous phase such as a hydrophobic oil or polymer. A third category is a water-in-oil-in-water (W/O/W) emulsion. These types of emulsions include a polar dispersed phase in a non-polar continuous phase which is, in turn, dispersed in a polar continuous phase. For example, W/O/W emulsions may include water droplets entrapped within larger oil droplets that in turn are dispersed in a continuous water phase. A fourth category is a water-in-water (W/W) emulsion. These types of emulsions include aqueous solvated molecules, e.g., particles of the disclosure, in a continuous aqueous solution wherein both the aqueous solvated molecules and the continuous aqueous solution include different molecules that are water-soluble. Without intending to be bound by any particular theory, it is believed that the aforementioned types of emulsions depend on hydrogen bonding, pi stacking, and/or salt bridging of both the dispersed and continuous phases. In this disclosure, the emulsion may be further defined as any one of these four types of emulsions.

As is also known in the art, emulsions may be, to a certain degree, unstable. Typically, there are three types of instability including (i) flocculation, where particles of the dispersed phase form clumps in the continuous phase, (ii) creaming or sedimentation, where the particles of the dispersed phase concentrate respectively towards a top or bottom of the continuous phase, and (iii) breaking and coalescence, where the particles of the dispersed phase coalesce and form a layer of liquid in the continuous phase. The instant emulsion may exhibit one or more of these types of instability. Typically, these types of instability are minimized.

As is also known in the art, emulsions typically have two different types of viscosities, a total viscosity and a viscosity of the dispersed phase. The emulsion of the instant disclosure typically has a total viscosity of at least 10 centistokes at a temperature of 25° C. In various embodiments, the emulsion has a total viscosity of 10 to 50 centistokes, more typically from about 10 to 500, or from about 50 to 200, centistokes at a temperature of 25° using a Brookfield rotating disc viscometer equipped with a thermal cell and an SC4-31 spindle operated at a constant temperature of 25° C. and a rotational speed of 5 rpm. The viscosity of the dispersed phase is not limited and is not believed to affect the total viscosity. In one embodiment, the dispersed phase is solid and has an infinite viscosity. All values and ranges of values therebetween the aforementioned values are hereby expressly contemplated in various non-limiting embodiments.

The emulsion may also include a surfactant or more than one surfactant. The surfactants may have the same or different HLBs from each other, as understood in the art and may each independently be a silicone or non-silicone surfactants. In various embodiments, the HLB of one or more surfactants may be from 5 to 20, from 6 to 19, from 7 to 18, from 8 to 17, from 9 to 16, from 10 to 15, from 11 to 14, or from 12 to 13. All values and ranges of values therebetween are also expressly contemplated in various non-limiting embodiments.

In various embodiments, one or more of the following surfactants is utilized, wherein the HLB is in parentheses: Genapol UD 050/UD 110 (HLB: 11.4/14.4); Brij L4/L23 (HLB: 9.7/16.9); Tergitol 15S5/15S15 (HLB: 10.5/15.4); Tween 20 (HLB: 16.7); and/or Lutensol XP-50-140 (HLB: 10-16), or combinations thereof.

In various embodiments, the emulsion includes the (first) surfactant and a second surfactant or multiple surfactants. Surfactants are also known as emulsifiers, emulgents, and tensides. Relative to this disclosure, the terminology "surfactant", "emulsifier", "emulgent", and "tenside" may be used interchangeably. Surfactants reduce a surface tension of a liquid by adsorbing at a liquid-gas interface. Surfactants also reduce interfacial tension between polar and non-polar molecules by adsorbing at a liquid-liquid interface. Without intending to be bound by any particular theory, it is believed that surfactants act at these interfaces and are dependent on various forces including, excluded volume repulsion forces, electrostatic interaction forces, van der waals forces, entropic forces, and steric forces. In the instant disclosure, the surfactant may be chosen or manipulated based on one or more of these forces.

The surfactant, first and second surfactants, or first/second/and multiple surfactants may independently be chosen from the group of non-ionic surfactants, cationic surfactants, anionic surfactants, amphoteric surfactants, and combinations thereof. Suitable non-ionic surfactants include, but are not limited to, alkylphenol akoxylates, ethoxylated and propoxylated fatty alcohols, alkyl polyglucosides and hydroxyalkyl polyglucosides, sorbitan derivatives, N-alkylglucamides, alkylene oxide block copolymers such as block copolymers of ethylene oxide, propylene oxide and/or butylene oxide, polyhydroxy and polyakoxy fatty acid derivatives, amine oxides, silicone polyethers, various polymeric surfactants based on polysaccharides, polymeric surfactants based on polyvinyl alcohol and polyacrylamide, and combinations thereof.

Suitable cationic surfactants include, but are not limited to, interface-active compounds including ammonium groups such as alkyldimethylammonium halides and compounds having the chemical formula RR'R''R'''N$^+$X$^-$ wherein R, R', R'', and R''' are independently chosen from the group of alkyl groups, aryl groups, alkylalkoxy groups, arylakoxy groups, hydroxyalkyl(alkoxy) groups, and hydroxyaryl(alkoxy) groups and wherein X is an anion.

Suitable anionic surfactants include, but are not limited to, fatty alcohol sulfates and sulfates of ethoxylated fatty alcohols. Further non-limiting examples of suitable anionic surfactants include akanesulfonates, linear alkylbenzenesulfonates, linear alkyltoluenesulfonates, diphenyl sulfonates, and diphenylether sulfonates. Still further, the anionic surfactant may include olefinsulfonates and di-sulfonates, mixtures of akene- and hydroxyalkane-sulfonates or di-sulfonates, alkyl ester sulfonates, sulfonated polycarboxylic acids, alkyl glyceryl sulfonates, fatty acid glycerol ester sulfonates, alkylphenol polyglycol ether sulfates, paraffinsulfonates, alkyl phosphates, acyl isothionates, acyl taurates, acyl methyl taurates, alkylsuccinic acids, akenylsuccinic acids and corresponding esters and amides thereof, alkylsulfosuccinic acids and corresponding amides, mono- and di-esters of sulfosuccinic acids, acyl sarcosinates, sulfated alkyl polyglucosides, alkyl polyglycol carboxylates, hydroxyalkyl sarcosinates, and combinations thereof. Still further, polymeric anionic surfactants based on acrylic acid or sulfonated polystyrene, and combinations thereof, may also be used. Suitable ampholytic surfactants include, but are not limited to, aliphatic derivatives of secondary and/or tertiary amines which include an anionic group, betaine derivatives, and combinations thereof.

Additionally, the surfactant and/or first and second surfactants may independently include aliphatic and/or aromatic alkoxylated alcohols, LAS (linear alkyl benzene sulfonates), paraffin sulfonates, FAS (fatty alcohol sulfates), FAES (fatty alcohol ethersulfates), alkylene glycols, trimethylolpropane ethoxylates, glycerol ethoxylates, pentaerythritol ethoxylates, akoxylates of bisphenol A, and akoxylates of 4-methylhexanol and 5-methyl-2-propylheptanol, and combinations thereof. Further, the surfactant and/or first and second surfactants may include alkylpolysaccharides including linear or branched alkyl groups, linear or branched akenyl groups, alkylphenyl groups, alkylene groups, and/or combinations thereof. Typically, the surfactant is present in an amount of from 0.1 to 100, more typically of from 0.01 to 5, even more typically of from 0.5 to 5, and most typically of from 1.5 to 2.5, parts by weight per 100 parts by weight of the emulsion.

The emulsion may also include a thickener. As is known in the art, thickeners increase a viscosity of the emulsion at low shear rates while maintaining flow properties of the emulsion at higher shear rates. Suitable thickeners for use in the instant disclosure include, but are not limited to, polyalkylene oxides such as polyethylene oxide, polypropylene oxide, polybutylene oxide, and combinations thereof. In one embodiment, the thickener is chosen from the group of algenic acid and its derivatives, polyethylene oxide, polyvinyl alcohol, methyl cellulose, hydroxypropylmethyl cellulose, alkyl and hydroxyalkyl cellulose, carboxymethyl cellulose, hydroxyethyl cellulose, guar gum, gum arabic, gum ghatic, polyvinylpyrrolidone, starch, modified starch, tamarind gum, xanthan gum, polyacrylamide, polyacrylic acid, and combinations thereof.

The thickener may be combined with the liquid or any other component, before the emulsion is formed. Typically, the thickener is combined with the liquid before the emulsion is formed. In one embodiment, the thickener is combined with a liquid in which it is not soluble and this mixture is combined with the emulsion after it has been formed. Examples of such liquids include, but are not limited to, propylene glycol, ethylene glycol, glycerin, and combinations thereof. The thickener may be present in an amount of from 0.001 to 25, more typically of from 0.05 to 5, and most typically of from 0.1 to 0.5, parts by weight per 100 parts by weight of the emulsion.

The emulsion may also include additives. The additives may include, but are not limited to, conductivity-enhancing additives, salts, dyes, perfumes, preservatives, plasticizers, active ingredients, colorants, labeling agents, rust inhibitors, and combinations thereof. In one embodiment, the conductivity-enhancing additive includes an ionic compound. In another embodiment, the conductivity-enhancing additives are generally chosen from the group of amines, organic salts and inorganic salts, and mixtures thereof. Typical conductivity-enhancing additives include amines, quaternary ammonium salts, quaternary phosphonium salts, ternary sulfonium salts, and mixtures of inorganic salts with organic ligands. More typical conductivity-enhancing additives include quaternary ammonium-based organic salts including, but not limited to, tetrabutylammonium chloride, tetrabutylammonium bromide, tetrabutylammonium iodide, phenyltrimethylammonium chloride, phenyltriethylammonium chloride, phenyltrimethylammonium bromide, phenyltrimethylammonium iodide, dodecyltrimethylammonium chloride, dodecyltrimethylammonium bromide, dodecyltrimethylammonium iodide, tetradecyltrimethylammonium chloride, tetradecyltrimethylammonium bromide, tetradecytrimethylammonium iodide, hexadecyltrimethylammonium chloride, hexadecyltrimethylammonium bromide, and hexadecyltrimethylammonium iodide. The additive may be present in either the continuous or dispersed phase of the emulsion in any amount selected by one of skill in the art. In various embodiments, the amount of the additive is typically of from about 0.0001 to about 25%, more typically from about 0.001 to about 10%, and more typically from about 0.01 to about 1% based on the total weight of the particles.

In the emulsion, the weight ratio of the continuous phase, e.g. water, the aminosiloxane polymer, and one or more surfactants or other components is not particularly limited. However, in various embodiments, these three components are present in amounts as set forth below in weight percents:

| Aminosiloxane Polymer | 10 to 40 | 10 to 30 | 20 to 30 | 30 to 90 | 45 to 65 | 55 to 60 |
|---|---|---|---|---|---|---|
| One or More Surfactants | 2 to 25 | 5 to 20 | 10 to 15 | 0.5 to 5 | 1 to 5 | 2 to 5 |
| Other Components | 0.05 to 2 | 0.05 to 2 | 0.05 to 2 | 0.05 to 2 | 0.05 to 2 | 0.05 to 2 |
| Continuous Phase | Balance | Balance | Balance | Balance | Balance | Balance |
| Total | 100 parts by weight | 100 parts by weight | 100 parts by weight | 100 parts by weight | 100 parts by weight | 100 parts by weight |

Cross-Linked Aminosiloxane Polymer:

The cross-linked aminosiloxane polymer includes a first siloxane backbone, a second siloxane backbone, and at least one intramolecular structure cross-linking a silicon atom of the first siloxane backbone and a silicon atom of the second siloxane backbone. The terminology "cross-linked" describes that the first siloxane backbone and the second siloxane backbone as connected, in at least one place, by the intramolecular structure. Typically, the aminosiloxane polymer has two or more points of cross-linking or connection between the first and second siloxane backbones (i.e., intramolecular structures extending between the first and second siloxane backbones). In various embodiments, the aminosiloxane polymer includes 2 to 100, 5 to 100, 5 to 95, 10 to 90, 15 to 85, 20 to 80, 25 to 75, 30 to 70, 35 to 65, 40 to 60, 45 to 55, 50 to 55, 1, 2, 3, 4, 5, 6, 7, 8, 9, or 10, points of connection or cross linking between the first and second siloxane backbones. All values and ranges of values therebetween are also expressly contemplated in various non-limiting embodiments.

First and Second Siloxane Backbones:

The first and second siloxane backbones are not particularly limited so long as they each include at least one silicon atom. Each may independently include any M, D, T, and Q units. The symbols M, D, T, and Q represent the functionality of structural units of polyorganosiloxanes. The symbols are used in accordance with established understanding in the art. Thus, M represents the monofunctional unit $R^0_3SiO_{1/2}$. D represents the difunctional unit $R^0_2SiO_{2/2}$. T represents the trifunctional unit $R^0_2SiO_{3/2}$. Q represents the tetrafunctional unit $SiO_{4/2}$. Generic structural formulas of these units are shown below:

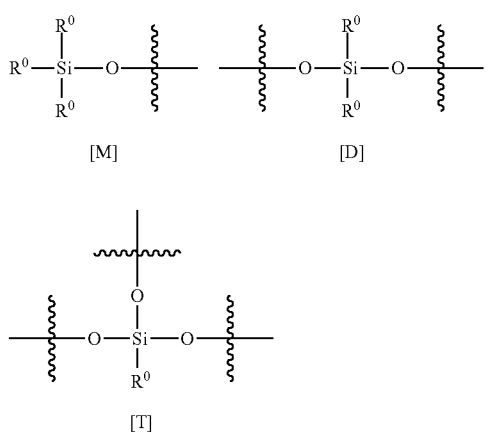

[M]  [D]

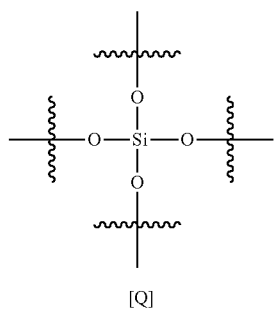

[T]

-continued

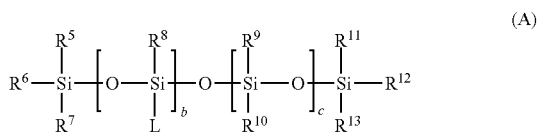

[Q]

In these structures/formulae, each $R^0$ may be any hydrocarbon, aromatic, aliphatic, alkyl, akenyl, or alkynl group. Similarly, the polyorganosiloxane is not particularly limited in molecular weight or viscosity and may be a fluid, gum, gel, etc.

In various embodiments, the first siloxane backbone has the chemical structure:

(A)

$$R^6-\underset{R^7}{\underset{|}{\overset{R^5}{\overset{|}{Si}}}}-\left[O-\underset{R^{10}}{\underset{|}{\overset{R^8}{\overset{|}{Si}}}}\right]_b-O-\left[\underset{R^{10}}{\underset{|}{\overset{R^9}{\overset{|}{Si}}}}-O\right]_c-\underset{R^{13}}{\underset{|}{\overset{R^{11}}{\overset{|}{Si}}}}-R^{12}$$

wherein each of $R^5$-$R^{13}$ is independently a hydrogen atom, a $C_1$-$C_{12}$ hydrocarbon group, a $C_2$-$C_{12}$ alkenyl group, a $C_6$-$C_{12}$ aromatic group, $R'(OR'')_m$ or a polyalkyleneoxy group, wherein each of R' and R" is independently an alkyl group, m is 1 to 3, b is from 1 to 100 and c is from 1 to 3,000, and wherein L is the intramolecular structure. In one embodiment, R" is methyl.

In various embodiments, m is 1, 2, or 3. In other embodiments, b can be from 1 to 100, from 5 to 95, from 10 to 90, from 15 to 85, from 20 to 80, from 25 to 75, from 30 to 70, from 35 to 65, from 40 to 60, from 45 to 55, or from 50 to 55. In still other embodiments, c can be from 1 to 3,000, from 1 to 2,500, from 1 to 2,000, from 1 to 1,500, from 1 to 1,000, from 1 to 500, from 1 to 100, from 200 to 600, from 250 to 550, from 300 to 500, from 350 to 450, or from 400 to 450. Moreover, all values and ranges of values therebetween, and all combinations of these values, are hereby expressly contemplated in various non-limiting embodiments.

In other embodiments, the second siloxane backbone has the chemical structure:

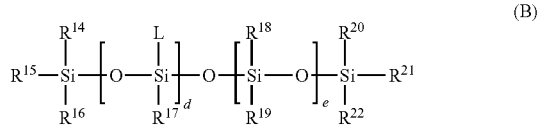

(B)

wherein each of $R^{14}$-$R^{22}$ is independently a hydrogen atom, a $C_1$-$C_{12}$ hydrocarbon group, a $C_2$-$C_{12}$ akenyl group, a $C_6$-$C_{12}$ aromatic group, R'(OR")$_m$ or a polyalkyleneoxy group, wherein each of R' and R" is independently an alkyl group, m is 1 to 3, d is from 1 to 100 and e is from 1 to 3,000, and wherein L is the intramolecular structure. The first and the second siloxane backbones can be the same or different from each other. In one embodiment, R" is methyl.

In various embodiments, m is 1, 2, or 3. In other embodiments, d can be from 1 to 100, from 5 to 95, from 10 to 90, from 15 to 85, from 20 to 80, from 25 to 75, from 30 to 70, from 35 to 65, from 40 to 60, from 45 to 55, or from 50 to 55. In still other embodiments, e can be from 1 to 3,000, from 1 to 2,500, from 1 to 2,000, from 1 to 1,500, from 1 to 1,000, from 1 to 500, from 1 to 100 from 200 to 600, from 250 to 550, from 300 to 500, from 350 to 450, or from 400 to 450. Moreover, all values and ranges of values therebetween, and all combinations of these values, are hereby expressly contemplated in various non-limiting embodiments.

In still other embodiments, one, more than one, or each of $R^5$-$R^{13}$ and/or $R^{14}$-$R^{22}$ is independently a hydrogen atom. Alternatively, one, more than one, or each of $R^5$-$R^{13}$ and/or $R^{14}$-$R^{22}$ can independently be a $C_1$-$C_{12}$ hydrocarbon group, e.g. methyl, ethyl, or propyl group, or any hydrocarbon group having up to 12 carbon atoms. More specifically, the hydrocarbon group can have 1, 2, 3, 4, 5, 6, 7, 8, 9, 10, 11, or 12 carbon atoms or any range of values therebetween. As is known in the art, hydrocarbons can include saturated hydrocarbons, unsaturated hydrocarbons having one or more double or triple bonds between carbon atoms, cycloalkanes having one or more carbon rings to which hydrogen atoms are attached, or aromatic hydrocarbons. In other embodiments, one, more than one, or each of $R^5$-$R^{13}$ and/or $R^{14}$-$R^{22}$ can independently be a $C_2$-$C_{12}$ akenyl group and have any number of carbon atoms or range of carbon atoms between 2 and 12. In further embodiments, one, more than one, or each of $R^5$-$R^{13}$ and/or $R^{14}$-$R^{22}$ can independently be a $C_6$-$C_{12}$ aromatic group and have any number of carbon atoms or range of carbon atoms between 6 and 12. In still other embodiments, one, more than one, or each of $R^5$-$R^{13}$ and/or $R^{14}$-$R^{22}$ can independently be R'(OR")$_m$ wherein each of R' and R" is independently an alkyl group and m is 1 to 3. This alkyl group may be, for example, methyl, ethyl, or propyl, or any hydrocarbon group having up to 12 carbon atoms, but is not limited in such a way. In still other embodiments, one, more than one, or each of $R^5$-$R^{13}$ and/or $R^{14}$-$R^{22}$ can independently be a polyalkyleneoxy group. Polyalkyleneoxy groups may be alternatively described as alkylene oxide groups, such as an ethylene oxide groups, propylene oxide groups, butylene oxide groups, etc. or combinations thereof. In still other embodiments, examples of suitable alkylene oxide groups that can be utilized include, but are not limited to, ethylene oxide groups, propylene oxide groups, butylene oxide groups, amylene oxide groups, mixtures thereof, alkylene oxide-tetrahydrofuran mixtures, epihalohydrins, and aralkylene styrenes, and combinations thereof. The structures of these compounds are known in the art. Moreover, all combinations of the aforementioned groups for the first and second siloxane backbones are hereby expressly contemplated in various non-limiting embodiments. It is contemplated that any one or more of $R^5$-$R^{13}$ may be substituted for any one or more of $R^{14}$-$R^{22}$. In other non-limiting embodiments, any one or more of $R^5$-$R^{13}$ may be the same as any one or more of $R^{14}$-$R^{22}$. In additional non-limiting embodiments, wherever any one or more of $R^5$-$R^{13}$ is shown herein, any one or more of $R^{14}$-$R^{22}$ may be substituted.

Intramolecular Structure:

The aminosiloxane polymer also includes at least one intramolecular structure cross-linking a silicon atom of the first siloxane backbone and a silicon atom of the second siloxane backbone, as first introduced above. The intramolecular structure has the chemical structure:

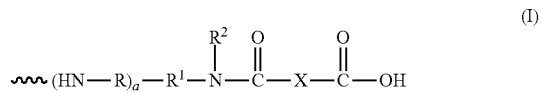

(I)

wherein X is chosen from the following groups;

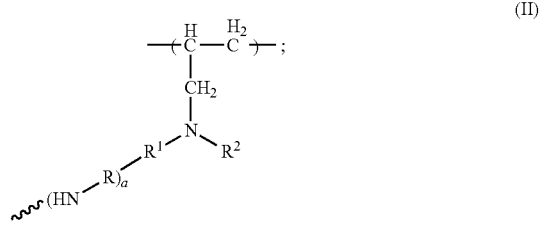

(II)

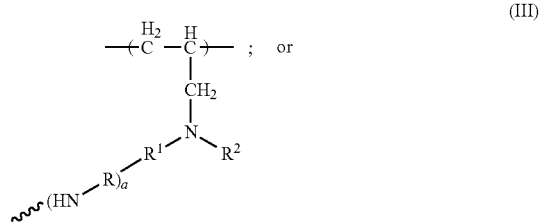

(III)

-continued

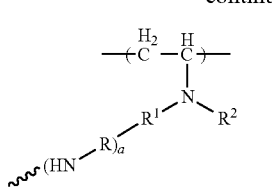
(IV)

wherein each R is independently a $C_1$-$C_{10}$ hydrocarbon group, each $R^1$ is independently a $C_1$-$C_{10}$ hydrocarbon group, each $R^2$ is independently a hydrogen atom, OH, a $C_1$-$C_{12}$ hydrocarbon group, a phenyl group, R'(OR")$_m$ wherein m is 1 to 3; or R'OH, wherein each of R' and R" is independently an alkyl group, and wherein a is 0 or 1.

More specifically, and in various embodiments, the intramolecular structure can have the following chemical structures:

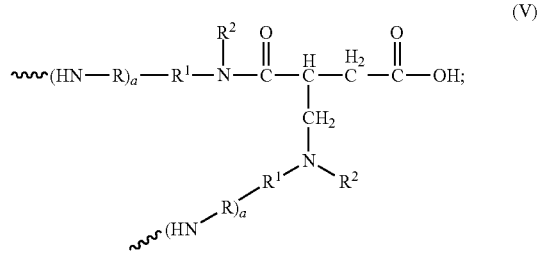
(V)

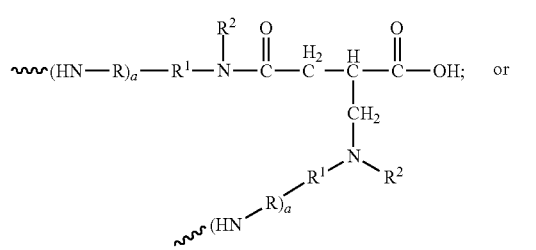
(VI)

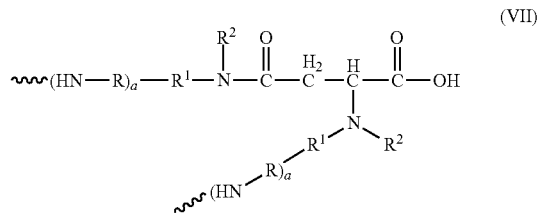
(VII)

In various embodiments, each R is independently a $C_1$-$C_{10}$ hydrocarbon group, e.g. methyl, ethyl, or propyl group, or any hydrocarbon group having up to 10 carbon atoms, for example, as described above. More specifically, R can have 1, 2, 3, 4, 5, 6, 7, 8, 9, or 10 carbon atoms or any range of values therebetween. Moreover, a is 0 or 1, such that (R—NH) is optional. Said differently, if a is 0, then (R—NH) is not present.

$R^1$ may be any of the groups described above relative to R and may be independently chosen from R. In other words, R and $R^1$ may be the same or different from one another. In various embodiments, one or both of $R^2$ is a hydrogen atom. In additional embodiments, one or both of $R^2$ is OH. In other embodiments, one or both of $R^2$ is independently a $C_1$-$C_{12}$ hydrocarbon group that can have 1, 2, 3, 4, 5, 6, 7, 8, 9, 10, 11, or 12, carbon atoms or any range of values therebetween.

The hydrocarbon group may be as described above. In still other embodiments, one or both of $R^2$ is a phenyl group. In other embodiments, one or both of $R^2$ is R'(OR")$_m$ wherein m is 1, 2, or 3, wherein each of R' and R" is independently an alkyl group that may be any described above or may be different. In still other embodiments, one or both of $R^2$ is R'OH wherein R' is as previously described.

Reaction Product:

In one embodiment, the aminosiloxane polymer includes or is the reaction product of a polyorganosiloxane having an amino group and maleic anhydride and/or itaconic anhydride. In another embodiment, the aminosiloxane polymer includes or is the reaction product of a polyorganosiloxane having an amino group and a polyorganosiloxane that has an α,β-unsaturated carboxy acid amide group, which itself may result from the reaction of the polyorganosiloxane having the amino group and the maleic anhydride and/or the itaconic anhydride. The reaction of the polyorganosiloxane having the amino group and the maleic anhydride and/or the itaconic anhydride may proceed to form the aminosiloxane polymer but while doing may form the polyorganosiloxane that has an α,β-unsaturated carboxy acid amide group as an intermediate that itself reacts with another molecule of the starting polyorganosiloxane having the amino group.

Polyorganosiloxane Having an Amino Group:

The polyorganosiloxane having the amino group may be any in the art. For example, the polyorganosiloxane may include any M, D, T, and Q units, as described above.

In various embodiments, the polyorganosiloxane has the following chemical formula:

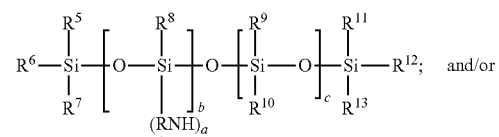
(VIII)

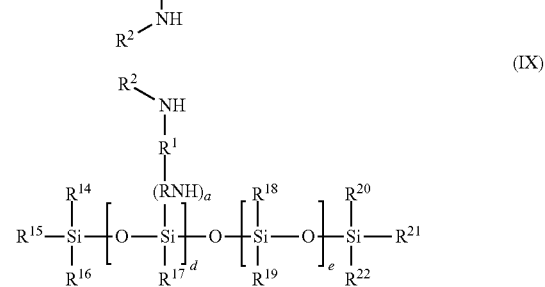
(IX)

wherein R, $R^1$, $R^2$, $R^5$-$R^{22}$, a, b, c, d, and e are as described above. Mixtures or combinations may also be used.

The polyorganosiloxane that has the α,β-unsaturated carboxy acid amide group is not particularly limited. The α,β-unsaturation may be relative to an amide group or to a carboxylic acid group. In one embodiment, this polyorganosiloxane is described as having an α,β-unsaturated carboxylic acid amide group.

In various embodiments, the polyorganosiloxane that has the α,β-unsaturated carboxy acid amide group has the chemical formula:

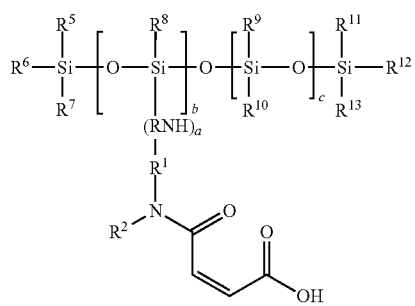

(X)

wherein R, $R^1$, $R^2$, $R^5$-$R^{13}$, a, b, and c are as described above.

In other embodiments, the polyorganosiloxane that has the α,β-unsaturated carboxy acid amide group is the reaction product of a second polyorganosiloxane and maleic anhydride, wherein the second polyorganosiloxane has an amino group. The second polyorganosiloxane having the amino group may be the same as the polyorganosiloxane described above or may be different. In other embodiments, the second polyorganosiloxane having the amino group has the formula as described above. Maleic anhydride has the following formula and structure:

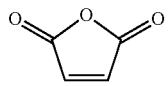

(XI)

maleic anhydride
Chemical Formula: $C_4H_2O_3$

Due to the symmetry of maleic anhydride, typically only one major product will be formed in the aforementioned reactions as shown in the reaction scheme below:

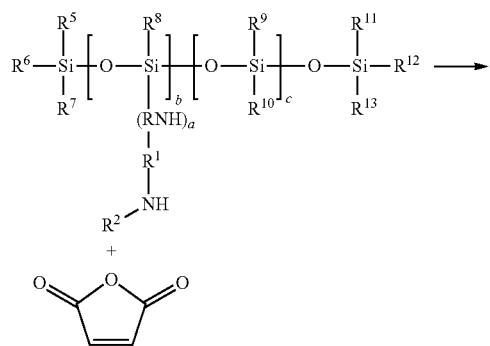

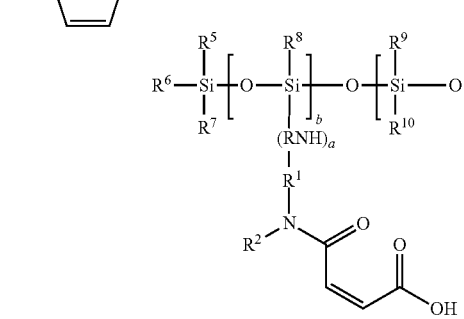

wherein R, $R^1$, $R^2$, $R^5$-$R^{13}$, a, b, and c are as described above.

In other embodiments, the polyorganosiloxane that has the α,β-unsaturated carboxy acid amide group is the reaction product of the second polyorganosiloxane and itaconic anhydride, wherein the second polyorganosiloxane has an amino group. The second polyorganosiloxane having the amino group may be the same as the polyorganosiloxane described above or may be different. In other embodiments, the second polyorganosiloxane having the amino group has the formula as described above. Itaconic anhydride has the following formula and structure:

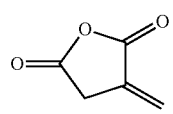

(XII)

itaconic anhydride
Chemical Formula: $C_5H_4O_3$

When utilizing the asymmetrical itaconic anhydride, various major products may be formed, as is understood in the art and is shown in non-limiting examples below. Accordingly, the polyorganosiloxane that has the α,β-unsaturated carboxy acid amide group may have the following structures and may be formed using the following reaction scheme:

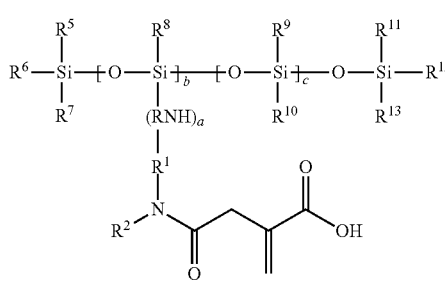

(XIII)

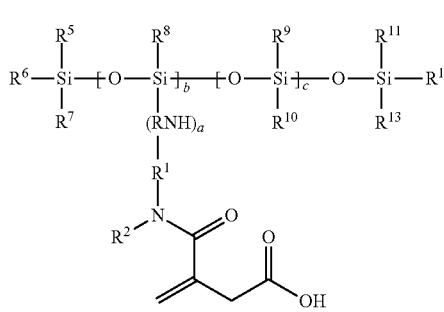

(XIV)

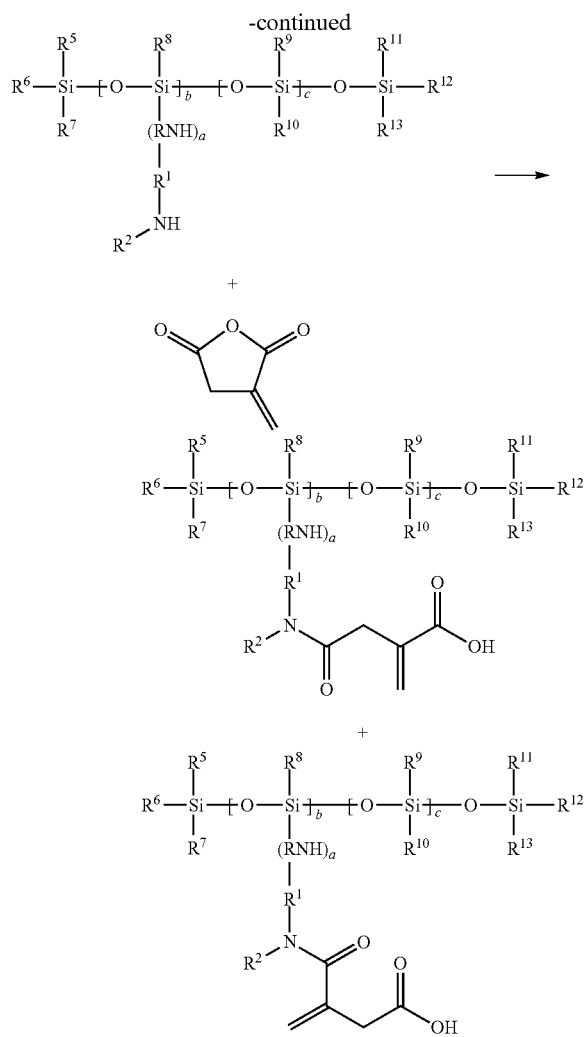

wherein R, $R^1$, $R^2$, $R^5$-$R^{13}$, a, b, and c are as described above.

In still other embodiments, the maleic anhydride and/or the itaconic anhydride reacts in an amount of from 0.01 to 0.5, 0.1 to 0.4, or from 0.01 to 0.4 moles, or 0.01 to 0.33 moles, per 1 mole of the amino group of the second organopolysiloxane, or any value or range of values therebetween.

Cross-Linked Aminosiloxane Polymer:

Referring back to the aminosiloxane polymer itself, it is not particularly limited except as described herein in various embodiments. For example, the weight or number average molecular weight of the aminosiloxane polymer is not particularly limited. In various embodiments, the aminosiloxane polymer has a weight average molecular weight of from 310 to 300,000, from 10,000 to 100,000, from 15000 to 60,000, g/mol. Similarly, the degree of polymerization of the first and second siloxane backbones of the aminosiloxane polymer is not particularly limited. In various embodiments, the degree of polymerization is from 1 to 3,000, from 100 to 1000, or from 200 to 600. Even further, the ratio of b and c, and/or d and e, of the siloxane backbones is not particularly limited. In various embodiments, the ratio is from 0.01 to 1, from 0.01 to 0.5, or from 0.01 to 0.2.

Moreover, the viscosity of the polymer is not particularly limited. In various embodiments, the viscosity is from 10 to 100,000, from 100 to 10,000, or from 500 to 5,000, cP as measured using a Brookfield viscometer at 25° C.

Method of Forming the Emulsion and the Aminosiloxane Polymer:

This disclosure also provides a method of forming the emulsion and a method of forming the cross-linked aminosiloxane polymer.

The method of forming the aminosiloxane polymer includes the steps of providing the polyorganosiloxane having the amino group, providing the maleic anhydride and/or the itaconic anhydride, and combining the maleic anhydride and/or itaconic anhydride and the polyorganosiloxane having the amino group to form the cross-linked aminosiloxane polymer. Each of the steps of providing may be further defined as any known in the art. For example, each of the aforementioned components may be provided in a vessel, reactor, etc. and may be provided in a batch-wise or continuous manner and at any appropriate temperature, pressure, rate, and amount, as is understood by those of skill in the art.

In one embodiment, the step of providing the polyorganosiloxane having the amino group is further defined as providing a first emulsion including a first continuous phase and a first dispersed phase including the polyorganosiloxane having the amino group. The first continuous phase may be any type of continuous phase described above. Moreover, the first emulsion may be any type of emulsion described above.

Moreover, the step of combining the maleic anhydride and/or itaconic anhydride and the polyorganosiloxane having the amino group to form the cross-linked aminosiloxane polymer may be further defined as adding the first emulsion to the maleic anhydride and/or itaconic anhydride, or vice versa, e.g. to form a second emulsion. Typically, the second emulsion includes a second continuous phase and a second dispersed phase. Upon formation of the second emulsion, the second dispersed phase typically includes or is the polyorganosiloxane having the amino group and the maleic anhydride and/or itaconic anhydride. After in-situ reaction, the second dispersed phase then typically includes or is the aminosiloxane polymer. The second continuous phase may be any type of continuous phase described above. Moreover, the second emulsion may be any type of emulsion described above.

The method may also include heating the first and/or second emulsions at or to a temperature of 20 to 90, 20 to 80, 25 to 75, 30 to 70, 35 to 65, 40 to 60, 45 to 55, or 50 to 55, ° C. to form the aminosiloxane polymer in-situ in the second emulsion. The terminology "in-situ" describes an embodiment wherein the aminosiloxane polymer is formed in the emulsion, e.g. in the second dispersed phase of the second emulsion. However, it is contemplated that the aminosiloxane polymer may be formed apart from an emulsion and later emulsified using any technique known in the art.

In various embodiments, the polyorganosiloxane having the amino group is present in the first dispersed phase of the first emulsion in an amount of from 10 to 90, 10 to 80, 10 to 70, 15 to 65, 20 to 60, 25 to 55, 30 to 50, 35 to 45, or 40 to 45, parts by weight per 100 parts by weight of the first emulsion. In other embodiments, the polyorganosiloxane having the amino group is present in the second dispersed phase of the second emulsion in an amount of from 10 to 90, 10 to 80, 10 to 70, 15 to 65, 20 to 60, 25 to 55, 30 to 50, 35 to 45, or 40 to 45, parts by weight per 100 parts by weight of the second emulsion. All values and ranges of values therebetween the aforementioned values are hereby expressly contemplated in various non-limiting embodiments.

In still other embodiments, the maleic anhydride and/or itaconic anhydride is present in the second dispersed phase of the second emulsion in an amount of from in an amount of from 10 to 90, 10 to 80, 10 to 70, 15 to 65, 20 to 60, 25 to 55, 30 to 50, 35 to 45, or 40 to 45, parts by weight per 100 parts by weight of the second emulsion. In addition, after formation (e.g. in-situ formation in the second dispersed phase of the second emulsion), the aminosiloxane polymer may be present in the second emulsion in amount of from 10 to 90, 10 to 80, or 20 to 70, parts by weight per 100 parts by weight of the second emulsion. The amount of the aminosiloxane polymer in the second emulsion may be as described above. All values and ranges of values therebetween the aforementioned values are hereby expressly contemplated in various non-limiting embodiments.

In still other embodiments, the step of providing the maleic anhydride and/or itaconic anhydride is further defined as providing 0.01 to 0.33, 0.01 to 0.4, from 0.01 to 0.5, from 0.01 to 0.45, or from 0.1 to 0.4 moles of the maleic anhydride and/or itaconic anhydride per 1 mole of the amino group of the polyorganosiloxane.

In one embodiment, the step of providing the maleic anhydride and/or the itaconic anhydride is further defined as providing the maleic anhydride in the absence of the itaconic anhydride. In another embodiment, the step of providing the maleic anhydride and/or the itaconic anhydride is further defined as providing the itaconic anhydride in the absence of the maleic anhydride. Each may be present in its own independent emulsion, e.g. in an independent dispersed phase in an emulsion that is independent from any emulsion described above.

In other embodiments, the method includes the step of providing a polydialkylsiloxane independently from the maleic anhydride, the itaconic anhydride, and/or the polyorganosiloxane having the amino group. Alternatively, the polydialkylsiloxane may be provided with the maleic anhydride, the itaconic anhydride, and/or the polyorganosiloxane having the amino group. The polydialkylsiloxane may act as a diluent in any emulsion described herein and may facilitate or improve film forming ability and/or physical properties of the film when formed on a substrate. In still other embodiments, the polydialkylsiloxane may be added or present in any step of the method or emulsion described herein.

The polydialkylsiloxane may be a single polydialkylsiloxane or a combination of two or more polydialkylsiloxanes. The polydialkylsiloxane is not particularly limited and, in various embodiments, has a weight average molecular weight ($M_w$) of up to 1,000,000 g/mol. In still other embodiments, the polydialkylsiloxane has a $M_w$ of 100,000 to 1,000,000, from 100,000 to 250,000, from 100,000 to 500,000, from 100,000 to 750,000, from 250,000 to 1,000,000, from 250,000 to 750,000, from 250,000 to 500,000, from 500,000 to 750,000, or from 750,000 to 1,000,000, g/mol. A mixture of a polydialkylsiloxane having a Mw of up to 1,000,000 g/mol and aminosiloxane polymer may also be utilized in this disclosure, e.g. in the emulsion or the method, wherein a ratio of the polydialkylsiloxane to the aminosiloxane polymer is from 0.1 to 100. All values and ranges of values between the aforementioned values are hereby expressly contemplated in various non-limiting embodiments.

In various embodiments, the polydialkylsiloxane has the general formula:

wherein $R^a$ is an alkyl group having 1 to 30 carbon atoms, $R^b$ may be an $R^a$ alkyl group or a hydroxy group, and the subscript "x" represents the degree of polymerization and is greater than 1000. In various embodiments, the polydialkylsiloxane is a trimethylsiloxy terminated polydimethylsiloxane fluid having a degree of polymerization (x) that is sufficient to provide a polydimethylsiloxane fluid viscosity of at least 50,000 mm/s (or 50,000 centistokes, abbreviated as cS) at 23° C. Alternatively, (x) is sufficient to provide a polydimethylsiloxane fluid viscosity of at least 100,000 mm/s at 23° C. Alternatively, (x) is sufficient to provide a polydimethylsiloxane fluid viscosity of at least 500,000 mm/s at 23° C. Non-limiting commercial products of trimethylsiloxy terminated polydimethylsiloxane fluids suitable for use herein as the polydialkylsioxane include Dow Corning 200® fluids having a viscosity of at least 50,000 centistokes. All values and ranges of values between the aforementioned values are hereby expressly contemplated in various non-limiting embodiments.

Any of the aforementioned emulsions may be formed by any suitable means known in the art and typically includes combining a liquid continuous phase with an immiscible dispersed phase. The liquid continuous phase may be any described above. The step of forming the emulsion may include emulsifying any one or more of the aforementioned compounds. A surfactant and/or thickener may be added to the liquid continuous phase prior to, concurrent with, or after combination with the aminosiloxane polymer and/or particles.

In various embodiments, one or more of the aforementioned emulsions is formed by simple agitation to form a coarse mixture, e.g. a water in polymer mixture. This mixture may then be emulsified. During emulsification, the coarse mixture can be inverted into an emulsion. The emulsification can be accomplished by conventional methods such as with ribbon mixers, plow mixers, fluidizing paddle mixers, sigma blade mixers, tumble blenders, vortex mixers, feed mixers, vertical mixers, horizontal mixers, and combinations thereof.

The in-situ reaction of the polyorganosiloxane having the amino group and the maleic anhydride and/or itaconic anhydride may occur via the following reaction schemes but is not limited as such:

Reaction Scheme One:

Polyorganosiloxane Having The Amine Group + Itaconic Anhydride

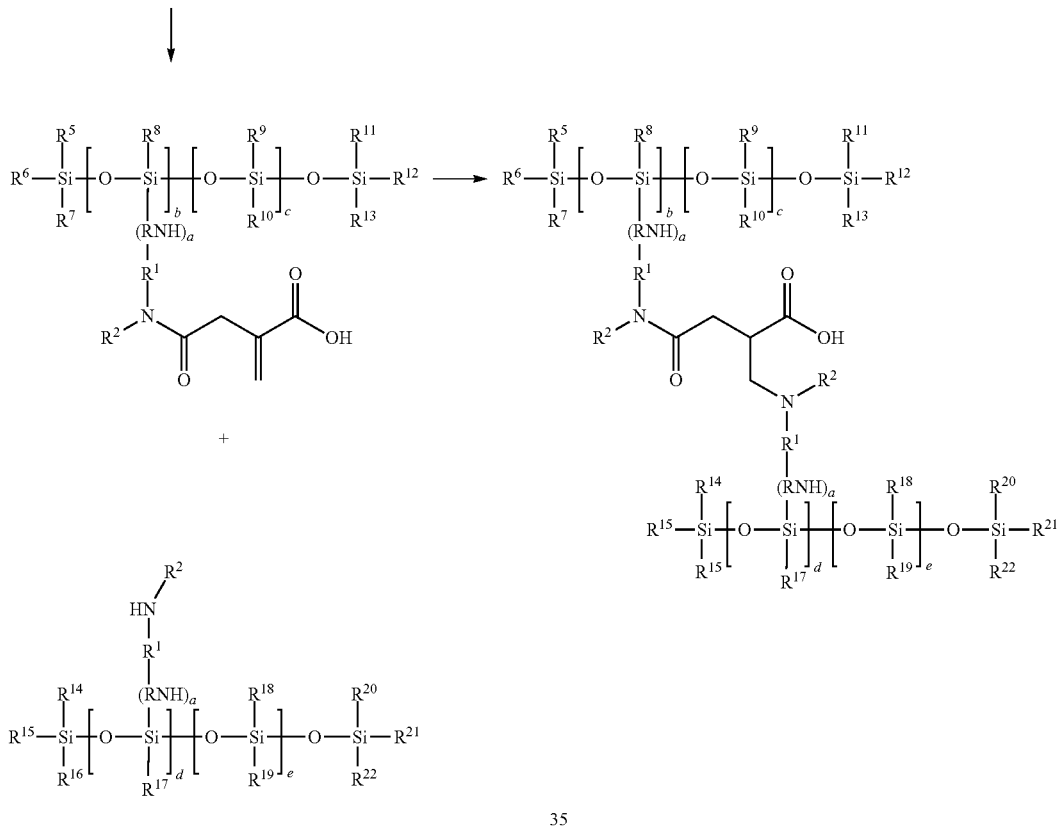

wherein R, $R^1$, $R^2$, $R^5$-$R^{22}$, a, b, c, d, and e are as described above.

Reaction Scheme Two:

Polyorganosiloxane Having The Amine Group + Itaconic Anhydride

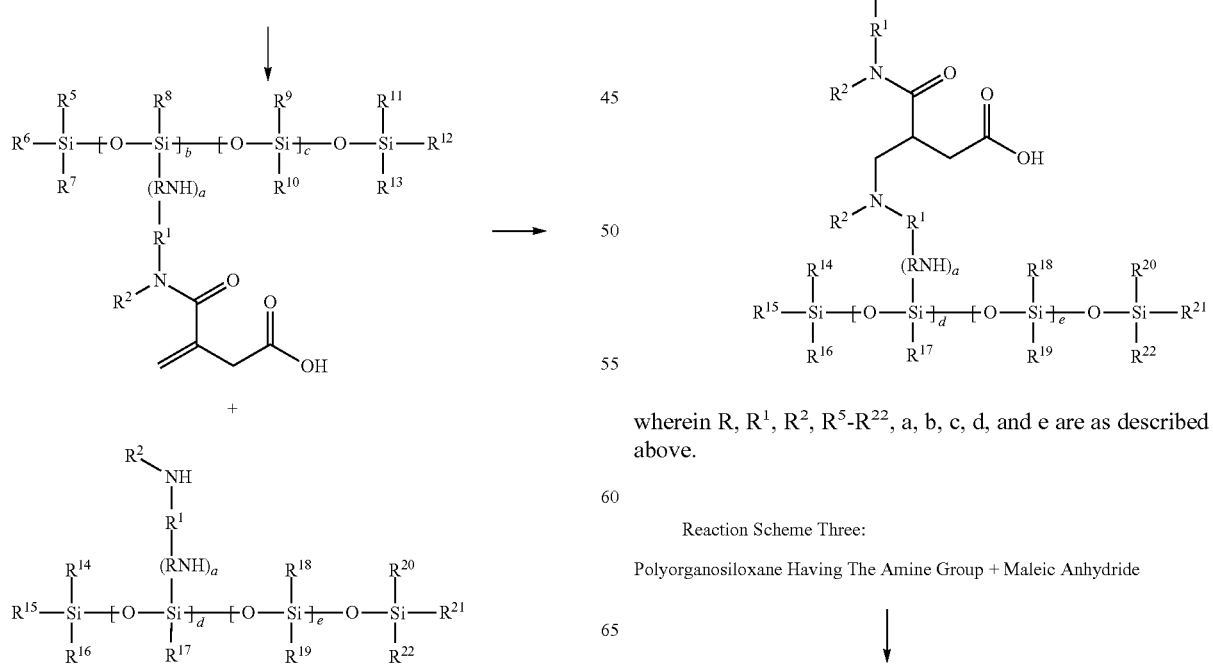

wherein R, $R^1$, $R^2$, $R^5$-$R^{22}$, a, b, c, d, and e are as described above.

Reaction Scheme Three:

Polyorganosiloxane Having The Amine Group + Maleic Anhydride

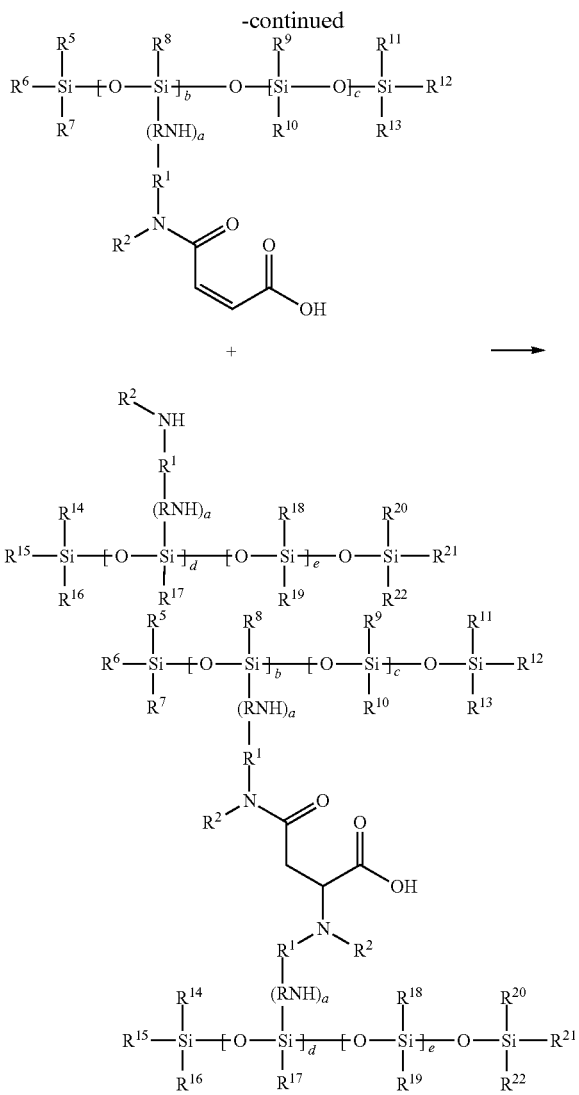

wherein R, $R^1$, $R^2$, $R^5$-$R^{22}$, a, b, c, d, and e are as described above.

When utilized, the maleic anhydride typically reacts with the polyorganosiloxane having the amino group in an amount of from 0.01 to 0.5, from 0.01 to 0.45, or from 0.1 to 0.4 moles, per mole of amino group. Moreover, when utilized, the itaconic anhydride typically reacts with the polyorganosiloxane having the amino group in an amount of from 0.01 to 0.5, from 0.01 to 0.45, or from 0.1 to 0.4 moles, per mole of amino group. Even further, if both the maleic anhydride and the itaconic anhydride are utilized, the total amount of the maleic anhydride and the itaconic anhydride that are utilized is typically of from 0.01 to 0.5, from 0.01 to 0.45, or from 0.1 to 0.4 moles, per mole of amino group. However, this disclosure is not limited to these amounts. All values and ranges of values therebetween the aforementioned values are hereby expressly contemplated in various non-limiting embodiments.

In various additional embodiments, this disclosure provides a film formed from the emulsion and/or including or being the aminosiloxane polymer. In other embodiments, this disclosure provides a use of the aminosiloxane polymer, the emulsion, or the film as a cosmetic ingredient. Alternatively, this disclosure provides a use of the aminosiloxane polymer, the emulsion, or the film as a fabric treating agent. Alternatively, this disclosure provides a use of the aminosiloxane polymer, the emulsion, or the film as a fiber treating agent or composition. Still further, this disclosure provides a cosmetic composition including the aminosiloxane polymer, the emulsion, or the film. This disclosure also provides a hair care composition including the aminosiloxane polymer, the emulsion, or the film. This disclosure further provides a fabric treating composition including the aminosiloxane polymer, the emulsion, or the film. This disclosure further provides a fiber treating composition including the aminosiloxane polymer, the emulsion, or the film.

Referring now to the film, the film may be of any dimensions relative to length, width, and thickness. Typically, the film is formed using the aminosiloxane polymer and/or the emulsion. For example, the aminosiloxane polymer and/or the emulsion may be poured onto a substrate and then dried to form the film. The substrate may be any in the art including plastic, wood, glass, polymers, metal, human skin, human hair, fabric, textiles, and the like.

The emulsion, film, and/or aminosiloxane polymer of the instant disclosure can be useful in many applications, for example in personal care applications such as on hair, skin, mucous membrane or teeth. In many of these applications, the emulsion, film, and/or aminosiloxane polymer is lubricious and improves properties of skin creams, skin care lotions, moisturizers, facial treatments such as acne or wrinkle removers, personal and facial cleansers, bath oils, perfumes, fragrances, colognes, sachets, sunscreens, pre-shave and after shave lotions, shaving soaps and shaving lathers. The emulsion, film, and/or aminosiloxane polymer can likewise be used in hair shampoos, hair conditioners, hair sprays, mousses, permanents, depilatories, and cuticle coats, for example to provide styling and conditioning benefits. In cosmetics, the emulsion, film, and/or aminosiloxane polymer may function as a leveling and spreading agent for pigment in make-ups, color cosmetics, foundations, blushes, lipsticks, eye liners, mascaras, oil removers, color cosmetic removers and powders. The emulsion, film, and/or aminosiloxane polymer may also be useful as a delivery system for oil and water soluble substances such as vitamins, organic sunscreens, ceramides, pharmaceuticals and the like. When compounded into sticks, gels, lotions aerosols and roll-ons, the emulsion, film, and/or aminosiloxane polymer may impart a dry silky-smooth payout. The emulsion, film, and/or aminosiloxane polymer may also be mixed with deposition polymers, surfactants, detergents, antibacterials, anti-dandruffs, foam boosters, proteins, moisturizing agents, suspending agents, opacifiers, perfumes, coloring agents, plant extracts, polymers, and other conventional care ingredients. In one embodiment, the emulsion, film, and/or aminosiloxane polymer is included in a water based composition that is chosen from the group of cosmetic compositions, fabric treating compositions, hair care compositions, fiber care compositions, and combinations thereof. The emulsion, film, and/or aminosiloxane polymer may be used in personal care products in amounts of from 0.01 to about 50, and more typically in amounts of from 0.1 to 25, weight percent of a personal care product.

The emulsion, film, and/or aminosiloxane polymer may also be useful for numerous other applications such as textile fiber treatment, leather lubrication, fabric softening, release agents, water based coatings, oil drag reduction, particularly in crude oil pipelines, lubrication, facilitation of cutting cellulose materials, and in many other areas where silicones are conventionally used. The emulsion, film, and/or aminosiloxane polymer may also be used to reduce oil drag. The emulsion, film, and/or aminosiloxane polymer can also be used in antimicrobial applications, in preservatives, deodorants, wound dressings, and dentifrices, and as a catalyst in organic synthesis reactions. Further, the emulsion, film, and/or aminosiloxane polymer can be used in filters and solar cells. The emulsion also allows the particles of the aminosiloxane polymer to be handled easily and allows for quality checks on the particles to be performed efficiently and accurately. The emulsion also allows for a variety of types of compounds to be utilized to form particles that can be customized based on desired physical and chemical properties. The emulsion can also be effectively utilized in a variety of industries including in cosmetic and coating applications.

This disclosure also provides a personal care composition, which may also be described as a personal care product composition. The personal care composition includes the aminosiloxane polymer. The personal care composition may be in the form of a cream, a gel, a powder, a paste, or a freely pourable liquid. Generally, such compositions can be prepared at room temperature if no solid materials at room temperature are present in the compositions, using simple propeller mixers, Brookfield counter-rotating mixers, or homogenizing mixers. No special equipment or processing conditions are typically required. Depending on the type of form made, the method of preparation will be different, but such methods are well known in the art.

The personal care composition may be functional with respect to the portion of the body to which it is applied, cosmetic, therapeutic, or some combination thereof. Conventional examples of such products include, but are not limited to, antiperspirants and deodorants, skin care creams, skin care lotions, moisturizers, facial treatments such as acne or wrinkle removers, personal and facial cleansers, bath oils, perfumes, colognes, sachets, sunscreens, pre-shave and after-shave lotions, shaving soaps, and shaving lathers, hair shampoos, hair conditioners, hair colorants, hair relaxants, hair sprays, mousses, gels, permanents, depilatories, and cuticle coats, make-ups, color cosmetics, foundations, concealers, blushes, lipsticks, eyeliners, mascara, oil removers, color cosmetic removers, and powders, medicament creams, pastes or sprays including anti-acne, dental hygienic, antibiotic, healing promotive, nutritive and the like, which may be preventative and/or therapeutic. In general, the personal care composition may be formulated with a carrier that permits application in any conventional form, including but not limited to liquids, rinses, lotions, creams, pastes, gels, foams, mousses, ointments, sprays, aerosols, soaps, sticks, soft solids, solid gels, and gels. Suitable carriers are appreciated in the art.

The personal care composition can be used in or for a variety of personal, household, and healthcare applications. In particular, the aminosiloxane polymer and/or personal care compositions of the present disclosure may be used in the personal care products as described in U.S. Pat. Nos. 6,051,216, 5,919,441, 5,981,680; WO 2004/060271 and WO 2004/060101; in sunscreen compositions as described in WO 2004/060276; in cosmetic compositions also containing film-forming resins, as described in WO 03/105801; in the cosmetic compositions as described in US Pat. App. Pub. Nos. 2003/0235553, 2003/0072730 and 2003/0170188, in EP Pat. Nos. 1,266,647, 1,266,648, and 1,266,653, in WO 03/105789, WO 2004/000247 and WO 03/106614; as additional agents to those described in WO 2004/054523; in long wearing cosmetic compositions as described in US Pat. App. Pub. No. 2004/0180032; and/or in transparent or translucent care and/or make up compositions as described in WO 2004/054524, all of which are expressly incorporated herein by reference in various non-limiting embodiments.

The personal care composition and/or aminosiloxane polymer can be used by the standard methods, such as applying them to the human body, e.g. skin or hair, using applicators, brushes, applying by hand, pouring them and/or possibly rubbing or massaging the composition onto or into the body. Removal methods, for example for color cosmetics are also well known standard methods, including washing, wiping, peeling and the like. For use on the skin, the personal care composition and/or aminosiloxane polymer may be used in a conventional manner for example for conditioning the skin. An effective amount of the personal care composition and/or aminosiloxane polymer may be applied to the skin. Such effective amounts generally are from 1 $mg/cm^2$ to 3 $mg/cm^2$. Application to the skin typically includes working the personal care composition and/or aminosiloxane polymer into the skin. This method for applying to the skin typically includes the steps of contacting the skin with the personal care composition and/or aminosiloxane polymer in an effective amount and then rubbing the personal care composition and/or aminosiloxane polymer into the skin. These steps can be repeated as many times as desired to achieve the desired benefit.

Use of the personal care composition and/or aminosiloxane polymer on hair may use a conventional manner for conditioning hair. An effective amount of the personal care composition and/or aminosiloxane polymer for conditioning hair is applied to the hair. Such effective amounts generally are from 1 g to 50 g, typically from 1 g to 20 g. Application to the hair typically includes working the personal care composition and/or aminosiloxane polymer through the hair such that most or all of the hair is contacted with the personal care composition and/or aminosiloxane polymer. This method for conditioning the hair typically includes the steps of applying an effective amount of the personal care composition and/or aminosiloxane polymer to the hair, and then working the personal care composition and/or aminosiloxane polymer through the hair. These steps can be repeated as many times as desired to achieve the desired conditioning benefit.

Non-limiting examples of additives which may be formulated into the personal care composition, cosmetic composition, fabric treating composition, hair care composition, emulsion, film, and/or aminosiloxane polymer, or any other compositions described above, include, but are not limited to, additional silicones, anti-oxidants, cleansing agents, colorants, additional conditioning agents, deposition agents, electrolytes, emollients and oils, exfoliating agents, foam boosting agents, fragrances, humectants, occlusive agents, pediculicides, pH control agents, pigments, preservatives, biocides, other solvents, stabilizers, sun-screening agents, suspending agents, tanning agents, other surfactants, thickeners, vitamins, botanicals, waxes, rheology-modifying agents, anti-dandruff, anti-acne, anti-carie and wound healing-promotion agents.

The personal care composition, such as a shampoo or cleanser, emulsion, film, aminosiloxane polymer, and/or any other composition described above, may include at least one anionic detersive surfactant. This can be any of the well-known anionic detersive surfactants typically used in shampoo formulations. These anionic detersive surfactants can function as cleansing agents and foaming agents in the shampoo compositions. The anionic detersive surfactants are exemplified by alkali metal sulforicinates, sulfonated glyceryl esters of fatty acids such as sulfonated monoglycerides of coconut oil acids, salts of sulfonated monovalent alcohol esters such as sodium oleylisethianate, amides of amino sulfonic acids such as the sodium salt of oleyl methyl tauride, sulfonated products of fatty acids nitriles such as palmitonitrile sulfonate, sulfonated aromatic hydrocarbons such as sodium alpha-naphthalene monosulfonate, condensation products of naphthalene sulfonic acids with formaldehyde, sodium octahydroanthracene sulfonate, alkali metal alkyl sulfates such as sodium lauryl sulfate, ammonium lauryl sulfate or triethanol amine lauryl sulfate, ether sulfates having alkyl groups of 8 or more carbon atoms such as sodium lauryl ether sulfate, ammonium lauryl ether sulfate, sodium alkyl aryl ether sulfates, and ammonium alkyl aryl ether sulfates, alkylarylsulfonates having 1 or more alkyl groups of 8 or more carbon atoms, akybenzenesulfonic acid alkali metal salts exemplified by hexylbenzenesulfonic acid sodium salt, octylbenzenesulfonic acid sodium salt, decylbenzenesulfonic acid sodium salt, dodecylbenzenesulfonic acid sodium salt, cetylbenzenesulfonic acid sodium salt, and myristybenzenesulfonic acid sodium salt, sulfuric esters of polyoxyethylene alkyl ether including $CH_3(CH_2)_6CH_2O(C_2H_4O)_2SO_3H$, $CH_3(CH_2)_7CH_2O(C_2H_4O)_{3.5}SO_3H$, $CH_3(CH_2)_8CH_2O(C_2H_4O)_8SO_3H$, $CH_3(CH_2)_{19}CH_2O(C_2H_4O)_4SO_3H$, and $CH_3(CH_2)_{10}CH_2O(C_2H_4O)_6SO_3H$, sodium salts, potassium salts, and amine salts of alkylnaphthylsulfonic acid. Typically, the detersive surfactant is chosen from sodium lauryl sulfate, ammonium lauryl sulfate, triethanolamine lauryl sulfate, sodium lauryl ether sulfate, and ammonium lauryl ether sulfate. The anionic detersive surfactant can be present in the shampoo composition in an amount from 5 to 50 wt % and typically 5 to 25 wt % based on the total weight of the shampoo composition.

The personal care composition, emulsion, film, aminosiloxane polymer, and/or any other composition described above, may include at least one cationic deposition aid, typically a cationic deposition polymer. The cationic deposition aid is typically present at levels of from 0.001 to 5%, typically from 0.01 to 1%, more typically from 0.02% to 0.5% by weight. The cationic deposition polymer may be a homopolymer or be formed from two or more types of monomers. The molecular weight of the cationic deposition polymer is typically from 5,000 to 10,000,000, typically at least 10,000 and typically from 100,000 to 2,000,000. The cationic deposition polymers typically have cationic nitrogen containing groups such as quaternary ammonium or protonated amino groups, or a combination thereof. The cationic charge density has been found to need to be at least 0.1 meq/g, typically above 0.8 or higher. The cationic charge density should not exceed 4 meq/g, it is typically less than 3 and more typically less than 2 meq/g. The charge density can be measured using the Kjeldahl method and is within the above limits at the desired pH of use, which will in general be from 3 to 9 and typically from 4 to 8. It is contemplated that any and all values or ranges of values between those described above may also be utilized. The cationic nitrogen-containing group is typically present as a substituent on a fraction of the total monomer units of the cationic deposition polymer. Thus when the cationic deposition polymer is not a homopolymer it can include spacer noncationic monomer units. Such cationic deposition polymers are described in the CTFA Cosmetic Ingredient Directory, 3rd edition, which is expressly incorporated herein by reference in one or more non-limiting embodiments. Suitable cationic deposition aids include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers typically have $C_1$-$C_7$ alkyl groups, more typically $C_1$-$C_3$ alkyl groups. Other suitable spacers include vinyl esters, vinyl alcohol, maleic anhydride, propylene glycol and ethylene glycol. The cationic amines can be primary, secondary or tertiary amines, depending upon the particular species and the pH of the composition. In general secondary and tertiary amines, especially tertiary, are typical. Amine substituted vinyl monomers and amines can be polymerized in the amine form and then converted to ammonium by quaternization. Suitable cationic amino and quaternary ammonium monomers include, for example, vinyl compounds substituted with dialkyl aminoalkyl acrylate, dialkylamino alkylmethacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidine, e.g. alkyl vinyl imidazolium, and quaternized pyrrolidine, e.g. alkyl vinyl imidazolium, alkyl vinyl pyridinium, alkyl vinyl pyrrolidine salts. The alkyl portions of these monomers are typically lower alkyls such as the $C_1$-$C_7$ alkyls, more typically $C_1$ and $C_2$ alkyls. Suitable amine-substituted vinyl monomers for use herein include dialkylaminoalkyl acrylate, dialkylaminoalkyl methacrylate, dialkylaminoalkyl acrylamide, and dialkylaminoalkyl methacrylamide, wherein the alkyl groups are typically $C_1$-$C_7$ hydrocarbyls, more typically $C_1$-$C_3$, alkyls. The cationic deposition aids can include combinations of monomer units derived from amine- and/or quaternary ammonium-substituted monomer and/or compatible spacer monomers. Suitable cationic deposition aids include, for example: copolymers of 1-vinyl-2-pyrrolidine and 1-vinyl-3-methylimidazolium salt (e.g. Chloride salt) (referred to in the industry by the Cosmetic, Toiletry, and Fragrance Association, "CTFA" as Polyquatemium-16) such as those commercially available from BASF Wyandotte Corp. (Parsippany, N.J., USA) under the LUVIQUAT trade name (e.g. LUVIQUAT FC 370); copolymers of 1-vinyl-2-pyrrolidine and dimethylaminoethyl methacrylate (referred to in the industry by CTFA as Polyquaternium-11) such as those commercially from Gar Corporation (Wayne, N.J., USA) under the GAFQUAT trade name (e.g. GAFQUAT 755N); cationic diallyl quaternary ammonium-containing polymer including, for example, dimethyl diallylammonium chloride homopolymer and copolymers of acrylamide and dimethyl diallylammonium chloride, referred to in the industry (CTFA) as Polyquatemium 6 and Polyquaternium 7, respectively; mineral acid salts of aminoalkyl esters of homo- and co-polymers of unsaturated carboxylic acids having from 3 to 5 carbon atoms, as described in U.S. Pat. No. 4,009,256; and cationic polyacrylamides as described in UK Application No. 9403156.4 (WO95/22311), each of which is expressly incorporated herein in one or more non-limiting embodiments. Other cationic deposition aids that can be used include polysaccharide polymers, such as cationic cellulose derivatives and cationic starch derivatives. Cationic polysaccharide polymer materials suitable for use in compositions of the disclosure include those of the formula: A-O(R—N+R1R2R3X—) wherein: A is an anhydroglucose residual group, such as starch or cellulose anhydroglucose residual, R is an alkylene oxyalklene, polyoxyalkylene, or hydroxyalkylene group, or combination thereof, R1, R2 and R3 independently are alkyl, aryl, alkylaryl, arylalkyl, alkoxyalkyl, or alkoxyaryl groups, each group containing up to 18 carbon atoms, and the total number of carbon atoms for each cationic moiety (i.e., the sum of carbon atoms in R1, R2, R3) typically being 20 or less, and X is an anionic counterion. Cationic cellulose is available from Amerchol Corp. (Edison, N.J., USA) in their Polymer iR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the trade name Polymer LM-200. Other cationic deposition aids that can be used include cationic guar gum derivatives, such as guar hydroxypropyltrimonium chloride (Commercially available from Celanese Corp. in their Jaguar trademark series). Other materials include quaternary nitrogen-containing cellulose ethers (e.g. as described in U.S. Pat. No. 3,962,418), and copolymers of etherified cellulose and starch (e.g. as described in U.S. Pat. No. 3,958,581), each of which is expressly incorporated herein by reference in one or more non-limiting embodiments.

The personal care composition, emulsion, film, aminosiloxane polymer, and/or any other composition described above, may include a foam boosting agent. A foam boosting agent is an agent which increases the amount of foam available from a system at a constant molar concentration of surfactant, in contrast to a foam stabilizer which delays the collapse of a foam. Foam building is provided by adding to the aqueous media, a foam boosting effective amount of a foam boosting agent. The foam boosting agent is typically chosen from fatty acid alkanolamides and amine oxides. The fatty acid alkanolamides are exemplified by isostearic acid diethanolamide, lauric acid diethanolamide, capric acid diethanolamide, coconut fatty acid diethanolamide, linoleic acid diethanolamide, myristic acid diethanolamide, oleic acid diethanolamide, stearic acid diethanolamide, coconut fatty acid monoethanolamide, oleic acid monoisopropanolamide, and lauric acid monoisopropanolamide. The amine oxides are exemplified by N-cocodimethylamine oxide, N-lauryl dimethylamine oxide, N-myristyl dimethylamine oxide, N-stearyl dimethylamine oxide, N-cocamidopropyl dimethylamine oxide, N-tallowamidopropyl dimethylamine oxide, bis(2-hydroxyethyl) $C_{12-15}$ alkoxypropylamine oxide. Typically a foam boosting agent is chosen from lauric acid diethanolamide, N-lauryl dimethylamine oxide, coconut acid diethanolamide, myristic acid diethanolamide, and oleic acid diethanolamide. The foam boosting agent is typically present in the shampoo compositions in an amount from 1 to 15 wt % and more typically 2 to 10 wt % based on the total weight of the composition. The composition may further include a polyalkylene glycol to improve lather performance. Concentration of the polyalkylene glycol in the shampoo composition may be from 0.01% to 5%, typically from 0.05% to 3%, and more typically from 0.1% to 2%, by weight of the shampoo composition. The optional polyalkylene glycols are characterized by the general formula: $H(OCH_2CHR)_n$—OH wherein R is chosen from H, methyl, and combinations thereof. When R is H, these materials are polymers of ethylene oxide, which are also known as polyethylene oxides, polyoxyethylenes, and polyethylene glycols. When R is methyl, these materials are polymers of propylene oxide, which are also known as polypropylene oxides, polyoxypropylenes, and polypropylene glycols. When R is methyl, it is also understood that various positional isomers of the resulting polymers can exist. In the above structure, n has an average value of from 1500 to 25,000, typically from 2500 to 20,000, and more typically from 3500 to 15,000. Polyethylene glycol polymers useful herein are PEG-2M wherein R equals H and n has an average value of 2,000 (PEG-2M is also known as Polyox WSR9N-10, which is available from Union Carbide and as PEG-2,000); PEG-5M wherein R equals H and n has an average value of 5,000 (PEG-5M is also known as Polyox WSRO N-35 and Polyox WSRS N-80, both available from Union Carbide and as PEG-5,000 and Polyethylene Glycol 300,000); PEG-7M wherein R equals H and n has an average value of 7,000 (PEG-7M is also known as Polyox WSRO N-750 available from Union Carbide); PEG-9M wherein R equals H and n has an average value of 9,000 (PEG 9-M is also known as Polyox WSRS N-3333 available from Union Carbide); and PEG-14 M wherein R equals H and n has an average value of 14,000 (PEG-14M is also known as Polyox WSRO N-3000 available from Union Carbide). Other useful polymers include the polypropylene glycols and mixed polyethylene/polypropylene glycols.

The personal care composition, emulsion, film, aminosiloxane polymer, and/or any other composition described above, include a suspending agent at concentrations effective for suspending a silicone conditioning agent, or other water-insoluble material, in dispersed form in the personal care composition. Such concentrations may be from 0.1% to 10%, typically from 0.3% to 5.0%, by weight of the personal care composition. Suspending agents include crystalline suspending agents which can be categorized as acyl derivatives, long chain amine oxides, and combinations thereof, concentrations of which can be from 0.1% to 5.0%, typically from 0.5% to 3.0%, by weight of the shampoo compositions. These suspending agents are described in U.S. Pat. No. 4,741,855, which is expressly incorporated herein by reference in one or more non-limiting embodiments. These typical suspending agents include ethylene glycol esters of fatty acids typically having from 16 to 22 carbon atoms. More typical are the ethylene glycol stearates, both mono and distearate, but particularly the distearate containing less than 7% of the mono stearate. Other suitable suspending agents include alkanol amides of fatty acids, typically having from 16 to 22 carbon atoms, more typically 16 to 18 carbon atoms, typical examples of which include stearic monoethanolamide, stearic diethanolamide, stearic monoisopropanolamide and stearic monoethanolamide stearate. Other long chain acyl derivatives include long chain esters of long chain fatty acids (e.g. stearyl stearate, cetyl palmitate, etc.); glyceryl esters (e.g. glyceryl distearate) and long chain esters of long chain alkanol amides (e.g. stearamide diethanolamide distearate, stearamide monoethanolamide stearate). Long chain acyl derivatives, ethylene glycol esters of long chain carboxylic acids, long chain amine oxides, and alkanol amides of long chain carboxylic acids in addition to the typical materials listed above may be used as suspending agents. For example, it is contemplated that suspending agents with long chain hydrocarbyls having $C_8$-$C_{22}$ chains may be used. Other long chain acyl derivatives suitable for use as suspending agents include N,N-dihydrocarbyl amido benzoic acid and soluble salts thereof (e.g. Na, K), particularly N,N-di(hydrogenated) C16, C18 and tallow amido benzoic acid species of this family, which are commercially available from Stepan Company (Northfield, Ill., USA). Examples of suitable long chain amine oxides for use as suspending agents include alkyl (C16-C22) dimethyl amine oxides, e.g. stearyl dimethyl amine oxide. Other suitable suspending agents include xanthan gum at concentrations ranging from 0.3% to 3%, typically from 0.4% to 1.2%, by weight of the shampoo compositions. The use of xanthan gum as a suspending agent is described, for example, in U.S. Pat. No. 4,788,006, which is expressly incorporated herein by reference in one or more non-limiting embodiments. Combinations of long chain acyl derivatives and xanthan gum may also be used as a suspending agent in the shampoo compositions. Such combinations are described in U.S. Pat. No. 4,704,272, which is expressly incorporated herein by reference in one or more non-limiting embodiments. Other suitable suspending agents include carboxyvinyl polymers. Typical among these polymers are the copolymers of acrylic acid crosslinked with polyallyl-sucrose as described in U.S. Pat. No. 2,798,053, which is expressly incorporated herein by reference in one or more non-limiting embodiments. Examples of these polymers include Carbopol 934, 940, 941, and 956, available from B.F. Goodrich Company. Other suitable suspending agents include primary amines having a fatty alkyl moiety having at least 16 carbon atoms, examples of which include palmitamine or stearamine, and secondary amines having two fatty alkyl moieties each having at least 12 carbon atoms, examples of which include dipalmitoylamine or di(hydrogenated tallow)amine. Still other suitable suspending agents include di(hydrogenated tallow)phthalic acid amide, and crosslinked maleic anhydride-methyl vinyl ether copolymer. Other suitable suspending agents may be used in the shampoo compositions, including those that can impart a gel-like viscosity to the composition, such as water soluble or colloidally water soluble polymers like cellulose ethers (e.g. methylcellulose, hydroxybutyl methylcellulose, hyroxypropylcellulose, hydroxypropyl methylcellulose, hydroxyethyl ethylcellulose and hydroxyethylcellulose), guar gum, polyvinyl alcohol, polyvinyl pyrrolidone, hydroxypropyl guar gum, starch and starch derivatives, and other thickeners, viscosity modifiers, gelling agents, etc.

The personal care composition, emulsion, film, aminosiloxane polymer, and/or any other composition described above, may include one or more water-soluble emollients including, but not limited to, lower molecular weight aliphatic diols such as propylene glycol and butylene glycol; polyols such as glycerine and sorbitol; and polyoxyethylene polymers such as polyethylene glycol 200. The specific type and amount of water soluble emollient(s) employed will vary depending on the desired aesthetic characteristics of the composition, and is readily determined by one skilled in the art.

The personal care composition, emulsion, film, aminosiloxane polymer, and/or any other composition described above, may include one or more oils independent from the carrier fluid described above. The term "oil" as used herein describes any material which is substantially insoluble in water. Suitable oils include, but are not limited to, natural oils such as coconut oil; hydrocarbons such as mineral oil and hydrogenated polyisobutene; fatty alcohols such as octyldodecanol; esters such as $C_{12-15}$ alkyl benzoate; diesters such as propylene dipelarganate; and triesters, such as glyceryl trioctanoate and silicones especially cyclomethicone and dimethicone and combinations thereof. Suitable low viscosity oils have a viscosity of 5 to 100 mPA·s at 25° C., and are generally esters having the structure RCO—OR' wherein RCO represents the carboxylic acid radical and wherein OR' is an alcohol residue. Examples of these low viscosity oils include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, or combinations of octyldodecanol, acetylated lanolin alcohol, cetyl acetate, isododecanol, polyglyceryl-3-diisostearate, or combinations thereof. The high viscosity surface oils generally have a viscosity of 200-1,000,000 mPA·s at 25° C., typically a viscosity of 100,000-250,000 mPA·s. Surface oils include castor oil, lanolin and lanolin derivatives, triisocetyl citrate, sorbitan sesquioleate, $C_{10-18}$ triglycerides, caprylic/capric/triglycerides, coconut oil, corn oil, cottonseed oil, glyceryl triacetyl hydroxystearate, glyceryl triacetyl ricinoleate, glyceryl trioctanoate, hydrogenated castor oil, linseed oil, mink oil, olive oil, palm oil, illipe butter, rapeseed oil, soybean oil, sunflower seed oil, tallow, tricaprin, trihydroxystearin, triisostearin, trilaurin, trilinolein, trimyristin, triolein, tripalmitin, tristearin, walnut oil, wheat germ oil, cholesterol, or combinations thereof. The suggested ratio of low viscosity to high viscosity oils in the oil phase is 1:15 to 15:1, typically 1:10 to 10:1 respectively. The typical formulation of the disclosure includes 1 to 20% of a combination of low viscosity and high viscosity surface oils.

Mineral oils, such as liquid paraffin or liquid petroleum, or animal oils, such as perhydrosqualene or arara oil, or alternatively of vegetable oils, such as sweet almond, calophyllum, palm, castor, avocado, jojoba, olive or cereal germ oil, may be utilized. It is also possible to use esters of lanolic acid, of oleic acid, of lauric acid, of stearic acid or of myristic acid, for example; alcohols, such as oleyl alcohol, linoleyl or linolenyl alcohol, isostearyl alcohol or octyldodecanol; or acetylglycerides, octanoates, decanoates or ricinoleates of alcohols or of polyalcohols. It is alternatively possible to use hydrogenated oils which are solid at 25° C., such as hydrogenated castor, palm or coconut oils, or hydrogenated tallow; mono-, di-, tri- or sucroglycerides; lanolins; or fatty esters which are solid at 25° C.

The personal care composition, emulsion, film, aminosiloxane polymer, and/or any other composition described above, may include various waxes. The waxes generally have a melting point of from 35 to 120° C. at atmospheric pressure. Waxes in this category include synthetic wax, ceresin, paraffin, ozokerite, illipe butter, beeswax, carnauba, microcrystalline, lanolin, lanolin derivatives, candelilla, cocoa butter, shellac wax, spermaceti, bran wax, capok wax, sugar cane wax, montan wax, whale wax, bayberry wax, or combinations thereof. In one embodiment, the personal care composition includes 10-30% of a combination of waxes. Mention may be made, among the waxes capable of being used as non-silicone fatty substances, of animal waxes, such as beeswax; vegetable waxes, such as carnauba, candelilla, ouricury or japan wax or cork fibre or sugarcane waxes; mineral waxes, for example paraffin or lignite wax or microcrystalline waxes or ozokerites; synthetic waxes, including polyethylene waxes, and waxes obtained by the Fischer-Tropsch synthesis. Mention may be made, among the silicone waxes, of polymethylsiloxane alkyls, alkoxys and/or esters.

The personal care composition, emulsion, film, aminosiloxane polymer, and/or any other composition described above, may include a powder. The powder can be generally defined as dry, particulate matter having a particle size of 0.02-50 microns. The powder may be colored or non-colored (for example white). Suitable powders include bismuth oxychloride, titanated mica, fumed silica, spherical silica beads, polymethylmethacrylate beads, micronized teflon, boron nitride, acrylate polymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium carbonate, magnesium hydroxide, magnesium oxide, magnesium silicate, magnesium trisilicate, maltodextrin, montmorilionite, microcrystalline cellulose, rice starch, silica, talc, mica, titanium dioxide, zinc laurate, zinc myristate, zinc neodecanoate, zinc rosinate, zinc stearate, polyethylene, alumina, attapulgite, calcium carbonate, calcium silicate, dextran, kaolin, nylon, silica silylate, silk powder, serecite, soy flour, tin oxide, titanium hydroxide, trimagnesium phosphate, walnut shell powder, or combinations thereof. The powder may be surface treated with lecithin, amino acids, mineral oil, silicone oil, or various other agents either alone or in combination, which coat the powder surface and render the particles hydrophobic in nature.

The powder can also include or be an organic and/or inorganic pigment. Organic pigments are generally various aromatic types including azo, indigoid, triphenylmethane, anthraquinone, and xanthine dyes which are designated as D&C and FD&C blues, browns, greens, oranges, reds, yellows, etc. Inorganic pigments generally consist of insoluble metallic salts of certified color additives, referred to as the Lakes or iron oxides. A pulverulent coloring agent, such as carbon black, chromium or iron oxides, ultramarines, manganese pyrophosphate, iron blue, and titanium dioxide, pearlescent agents, generally used as a combination with colored pigments, or some organic dyes, generally used as a combination with colored pigments and commonly used in the cosmetics industry, can be added to the composition. In general, these coloring agents can be present in an amount by weight from 0 to 20% with respect to the weight of the personal care composition, emulsion, film, aminosiloxane polymer, and/or any other composition described above.

Pulverulent inorganic or organic fillers can also be added, generally in an amount by weight from 0 to 40% with respect to the weight of the personal care composition, emulsion, film, aminosiloxane polymer, and/or any other composition described above. These pulverulent fillers can be chosen from talc, micas, kaolin, zinc or titanium oxides, calcium or magnesium carbonates, silica, spherical titanium dioxide, glass or ceramic beads, metal soaps derived from carboxylic acids having 8-22 carbon atoms, non-expanded synthetic polymer powders, expanded powders and powders from natural organic compounds, such as cereal starches, which may or may not be crosslinked. The fillers may typically be present in a proportion of from 0 to 35% of the total weight of the composition, more typically 5 to 15%. Mention may be made in particular of talc, mica, silica, kaolin, nylon powders (in particular ORGASOL), polyethylene powders, Teflon, starch, boron nitride, copolymer microspheres such as EXPANCEL (Nobel Industrie), polytrap and silicone resin microbeads (TOSPEARL from Toshiba, for example).

The personal care composition, emulsion, film, aminosiloxane polymer, and/or any other composition described above, may include a sunscreen. Sunscreens typically absorb ultraviolet light between 290-320 nanometers (the UV-B region) such as, but not exclusively, para-aminobenzoic acid derivatives and cinnamates such as octyl methoxycinnamate and those which absorb ultraviolet light in the range of 320-400 nanometers (the UV-A region) such as benzophenones and butyl methoxy dibenzoylmethane. Some additional examples of sunscreens are 2-ethoxyethyl p-methoxycinnamate; menthyl anthranilate; homomethyl salicylate; glyceryl p-aminobenzoate; isobutyl p-aminobenzoate; isoamyl p-dimethylaminobenzoate; 2-hydroxy-4-methoxybenzophenones sulfonic acid; 2,2'-dihydroxy-4-methoxybenzophenone; 2-hydroxy-4-methoxybenzophenone; 4-mono and 4-bis(3-hydroxy-propyl)amino isomers of ethyl benzoate; and 2-ethylhexyl p-dimethylaminobenzoate. In various embodiments, the sunscreen is as described in EP-A-678, 292, which is expressly incorporated herein by reference in one or more non-limiting embodiments. In various embodiments, sunscreens include at least one carboxylic or better still sulphonic acid radical. This acid radical can be in free form or in partially or totally neutralized form. It is possible to use one or more hydrophilic screening agents containing acid functionality. As examples of acidic screening agents containing at least one SO3 H group, mention may be made more particularly of 3-benzylidine-2-camphorsulphonic derivatives. A particularly typical compound is benzene-1, 4-[di(3-methylidenecamphor-10-sulphonic acid)]. This screening agent is a broad-band screening agent capable of absorbing ultraviolet rays with wavelengths of between 280 nm and 400 nm, with absorption maxima of between 320 nm and 400 nm, in particular at 345 nm. It is used in acid form or salified with a base chosen from triethanolamine, sodium hydroxide and potassium hydroxide. In addition, it can be in cis or trans form. This screening agent is known under the trade name Mexoryl SX. Other specific examples are 4-(3-methylidenecamphor)benzenesulphonic acid, 3-benzylidenecamphor-10-sulphonic acid, 2-methyl-5-(3-methylidenecamphor)benzenesulphonic acid, 2-chloro-5-(3-methylidenecamphor)benzenesulphonic acid, 3-(4-methyl) benzylidenecamphor-10-sulphonic acid, (3-t-butyl-2-hydroxy-5-methyl)benzylidenecamphor-10-sulphonic acid, (3-t-butyl-2-hydroxy-5-methoxy)benzylidenecamphor-10-sulphonic acid, (3,5-di-tert-butyl-4-hydroxy)benzylidenecamphor-10-sulphonic acid, 2-methoxy-5-(3-methylidenecamphor)benzenesulphonic acid, 3-(4,5-methylenedioxy) benzylidenecamphor-10-sulphonic acid, 3-(4-methoxy) benzylidenecamphor-10-sulphonic acid, 3-(4,5-dimethoxy) benzylidenecamphor-10-sulphonic acid, 3-(4-n-butoxy) benzylidenecamphor-10-sulphonic acid, 3-(4-n-butoxy-5-methoxy)benzylidenecamphor-10-sulphonic acid, 2-[4-(camphormethylidene)phenyl]benzimidazole-5-sulphonic acid. Suitable compounds are described in U.S. Pat. No. 4,585,597, and FR 2,236,515, 2,282,426, 2,645,148, 2,430, 938 and 2,592,380, each of which is expressly incorporated herein by reference in one or more non-limiting embodiments. The screening agent containing a sulphonic group can also be a sulphonic derivative of benzophenone or 2-phenylbenzimidazole-5-sulphonic acid, having excellent photoprotective power in the UV-B radiation range and is sold under the trade name "Eusolex 232" by Merck, benzene-1,4-di(benzimidazol-2-yl-5-sulphonic acid), benzene-1,4-di(benzoxazol-2-yl-5-sulphonic acid). The hydrophilic screening agent(s) can be present in the final composition according to the disclosure in a content which can be from 0.1 to 20%, typically from 0.2 to 10%, by weight relative to the total weight of the personal care composition.

Additional lipophilic screening agents can be utilized such as those derived from dibenzoylmethane and more especially 4-tert-butyl-4'-methoxydibenzoylmethane, which effectively have a high intrinsic power of absorption. These dibenzoylmethane derivatives, which are products that are well known per se as UV-A active screening agents, are described in particular in French patent applications FR-A-2,326,405 and FR-A-2,440,933, as well as in European patent application EP-A-0,114,607, each of which is expressly incorporated herein by reference in one or more non-limiting embodiments. 4-(tert-butyl)-4'-methoxydibenzoylmethane is currently sold under the trade name "Parsol 1789" by Givaudan. Another dibenzoylmethane derivative which is typical according to the present disclosure is 4-isopropyldibenzoylmethane, this screening agent being sold under the name "Eusolex 8020" by Merck. Similarly octocrylene, a liquid lipophilic screening agent that is already known for its activity in the UV-B range is commercially available, and is sold in particular under the name "Uvinul N 539" by BASF. As another lipophilic (or liposoluble) screening agent which can be used in the disclosure, mention may also be made of p-methybenzylidenecamphor, which is also known as a UV-B absorber and is sold in particular under the trade name "Eusolex 6300" by Merck. The lipophilic screening agent(s) can be present in the composition according to the disclosure in a content which can be from 0.5 to 30%, typically from 0.5 to 20%, of the total weight of the personal care composition, emulsion, film, aminosiloxane polymer, and/or any other composition described above. Other examples of lipophilic or hydrophilic organic screening agents are described in patent application EP-A-0,487,404, which is expressly incorporated herein by reference in one or more non-limiting embodiments. The cosmetic and/or dermatological compositions according to the disclosure can also include pigments or alternatively nanopigments (average primary particle size: generally between 5 nm and 100 nm, typically between 10 and 50 nm) of coated or uncoated metal oxides, such as, for example, nanopigments of titanium oxide (amorphous or crystallized in rutile and/or anatase form), of iron oxide, of zinc oxide, of zirconium oxide or of cerium oxide, which are all photoprotective agents that are well known per se and which act by physically blocking (reflection and/or scattering) UV radiation. Standard coating agents are, moreover, alumina and/or aluminum stearate, and silicones. Such coated or uncoated metal oxide nanopigments are described in particular in patent applications EP-A-0,518,772 and EP-A-0,518,773, each of which is expressly incorporated herein by reference in one or more non-limiting embodiments.

A thickening agent may be utilized to provide a convenient viscosity for any composition described above. For example, viscosities of from 500 to 25,000 mm$^2$/s at 25° C. or more alternatively of from 3,000 to 7,000 mm$^2$/s at 25° C. may be obtained. Suitable thickening agents are exemplified by sodium alginate, gum arabic, polyoxyethylene, guar gum, hydroxypropyl guar gum, ethoxylated alcohols, such as laureth-4 or polyethylene glycol 400, cellulose derivatives exemplified by methylcellulose, methyihydroxypropylcellulose, hydroxypropylcellulose, polypropylhydroxyethylcellulose, starch, and starch derivatives exemplified by hydroxyethylamylose and starch amylose, locust bean gum, electrolytes exemplified by sodium chloride and ammonium chloride, and saccharides such as fructose and glucose, and derivatives of saccharides such as PEG-120 methyl glucose diolate or combinations of 2 or more of these. Alternatively the thickening agent is chosen from cellulose derivatives, saccharide derivatives, and electrolytes, or from a combination of two or more of the above thickening agents exemplified by a combination of a cellulose derivative and any electrolyte, and a starch derivative and any electrolyte. The thickening agent, where used is present in a shampoo composition, may provide a viscosity of from 500 to 25,000 mm$^2$/s at 25° C. Alternatively the thickening agent may be present in an amount from 0.05 to 10 wt % and alternatively 0.05 to 5 wt % based on the total weight of the personal care composition, emulsion, film, aminosiloxane polymer, and/or any other composition described above.

Stabilizing agents can also be used, e.g. in a water phase of an emulsion. Suitable water phase stabilizing agents can include alone or in combination one or more electrolytes, polyols, alcohols such as ethyl alcohol, and hydrocolbids. Typical electrolytes are alkali metal salts and alkaline earth salts, especially the chloride, borate, citrate, and sulfate salts of sodium, potassium, calcium and magnesium, as well as aluminum chlorohydrate, and polyelectrolytes, especially hyaluronic acid and sodium hyaluronate. When the stabilizing agent is, or includes, an electrolyte, it amounts to 0.1 to 5 wt % and more alternatively 0.5 to 3 wt % of the personal care composition, emulsion, film, aminosiloxane polymer, and/or any other composition described above. The hydrocolbids include gums, such as Xantham gum or Veegum and thickening agents, such as carboxymethyl cellulose. Polyols, such as glycerine, glycols, and sorbitols can also be used. Alternative polyols are glycerine, propylene glycol, sorbitol, and butylene glycol. If a large amount of a polyol is used, one need not add the electrolyte. However, it is typical to use a combination of an electrolyte, a polyol and a hydrocolloid to stabilize the water phase, e.g. magnesium sulfate, butylene glycol and Xantham gum.

Any of the aforementioned compositions may also be or include antiperspirant agents and deodorant agents such as Aluminum Chloride, Aluminum Zirconium Tetrachlorohydrex GLY, Aluminum Zirconium Tetrachlorohydrex PEG, Aluminum Chlorohydrex, Aluminum Zirconium Tetrachlorohydrex PG, Aluminum Chlorohydrex PEG, Aluminum Zirconium Trichlorohydrate, Aluminum Chlorohydrex PG, Aluminum Zirconium Trichlorohydrex GLY, Hexachlorophene, Benzalkonium Chloride, Aluminum Sesquichlorohydrate, Sodium Bicarbonate, Aluminum Sesquichlorohydrex PEG, Chlorophyllin-Copper Complex, Triclosan, Aluminum Zirconium Octachlorohydrate, and Zinc Ricinoleate.

The personal care composition, emulsion, film, aminosiloxane polymer, and/or any other composition described above, can be an aerosol in combination with propellant gases, such as carbon dioxide, nitrogen, nitrous oxide, volatile hydrocarbons such as butane, isobutane, or propane and chlorinated or fluorinated hydrocarbons such as dichlorodifluoromethane and dichlorotetrafluoroethane or dimethylether.

Silicone compositions, other than the present aminosiloxane polymer may also be included in the personal care composition, emulsion, film, aminosiloxane polymer, and/or any other composition described above. For example, such silicones include silicone fluids, gums, resins, elastomers; silicone surfactants and emulsifiers such as silicone polyethers, organofunctional silicones such as amino functional silicones and alkylmethylsiloxanes. Alkylmethylsiloxanes may be included in the present compositions. These siloxane polymers generally typically have the formula $Me_3SiO[Me_2SiO]_y[MeRSiO]_zSiMe_3$, in which R is a hydrocarbon group containing 6-30 carbon atoms, Me represents methyl, and the degree of polymerization (DP), i.e., the sum of y and z is 3-50. Both the volatile and liquid species of alkylmethysiloxanes can be used in the composition.

Silicone gums may also be included in the personal care composition, emulsion, film, aminosiloxane polymer, and/or any other composition described above. Suitable non-limiting gums include insoluble polydiorganosiloxanes having a viscosity in excess of 1,000,000 centistoke (mm$^2$/s) at 25° C., alternatively greater than 5,000,000 centistoke (mm$^2$/s) at 25° C. These silicone gums are typically sold as compositions already dispersed in a suitable solvent to facilitate their handling. Ultra-high viscosity silicones can also be included as optional ingredients. These ultra-high viscosity silicones typically have a kinematic viscosity greater than 5 million centistoke (mm$^2$/s) at 25° C. up to 20 million centistoke (mm²/s) at 25° C. Compositions of this type in are described for example in U.S. Pat. No. 6,013,682, which is expressly incorporated herein by reference in one or more non-limiting embodiments.

Silicone resins may also be included in the personal care composition, emulsion, film, aminosiloxane polymer, and/or any other composition described above. These resins are generally highly crosslinked polymeric siloxanes. Cross linking is typically obtained by incorporating trifunctional and/or tetrafunctional silanes with the monofunctional silane and/or difunctional silane monomers used during manufacture. The degree of cross linking required to obtain a suitable silicone resin will vary according to the specifics of silane monomer units incorporated during manufacture of the silicone resin. In general, any silicone having a sufficient level of trifunctional and tetrafunctional siloxane monomer units, and hence possessing sufficient levels of cross linking to dry down to a rigid or a hard film can be used. Commercially available silicone resins suitable for applications herein are generally supplied in an unhardened form in low viscosity, volatile or nonvolatile silicone fluids. The silicone resins may be incorporated into compositions of the disclosure in their non-hardened forms rather than as hardened resinous structures.

Silicone carbinol fluids may be included in the personal care composition, emulsion, film, aminosiloxane polymer, and/or any other composition described above. These materials can be commonly described as substituted hydrocarbyl functional siloxane fluids or resins and some are described in WO 03/101412 A2, which is expressly incorporated herein by reference in one or more non-limiting embodiments.

Water soluble or water dispersible silicone polyethers may also be included in the personal care composition, emulsion, film, aminosiloxane polymer, and/or any other composition described above. These are also known as polyalkylene oxide silicone copolymers, silicone poly(oxyalkylene) copolymers, silicone glycol copolymers, or silicone surfactants. These can be linear rake or graft type materials, or ABA type where the B is the siloxane polymer block, and the A is the poly(oxyalkylene) group. The poly (oxyalkylene) group can consist of polyethylene oxide, polypropylene oxide, or mixed polyethylene oxide/polypropylene oxide groups. Other oxides, such as butylene oxide or phenylene oxide are also possible.

Any of the personal care composition, emulsion, film, aminosiloxane polymer, and/or any other composition described above may also include a solvent such as (i) organic compounds, (ii) compounds containing a silicon atom, (iii) mixtures of organic compounds, (iv) mixtures of compounds containing a silicon atom, or (v) mixtures of organic compounds and compounds containing a silicon atom; used on an industrial scale to dissolve, suspend, or change the physical properties of other materials.

In general, the organic compounds are aromatic hydrocarbons, aliphatic hydrocarbons, alcohols, aldehydes, ketones, amines, esters, ethers, glycols, glycol ethers, alkyl halides, or aromatic halides. Representative of some common organic solvents are alcohols such as methanol, ethanol, 1-propanol, cyclohexanol, benzyl alcohol, 2-octanol, ethylene glycol, propylene glycol, and glycerol; aliphatic hydrocarbons such as pentane, cyclohexane, heptane, VM&P solvent, and mineral spirits; alkyl halides such as chloroform, carbon tetrachloride, perchloroethylene, ethyl chloride, and chlorobenzene; amines such as isopropylamine, cyclohexylamine, ethanolamine, and diethanolamine; aromatic hydrocarbons such as benzene, toluene, ethylbenzene, and xylene; esters such as ethyl acetate, isopropyl acetate, ethyl acetoacetate, amyl acetate, isobutyl isobutyrate, and benzyl acetate; ethers such as ethyl ether, n-butyl ether, tetrahydrofuran, and 1,4-dioxane; glycol ethers such as ethylene glycol monomethyl ether, ethylene glycol monomethyl ether acetate, diethylene glycol monobutyl ether, and propylene glycol monophenyl ether; ketones such as acetone, methyl ethyl ketone, cyclohexanone, diacetone alcohol, methyl amyl ketone, and diisobutyl ketone; petroleum hydrocarbons such as mineral oil, gasoline, naphtha, kerosene, gas oil, heavy oil, and crude oil; lubricating oils such as spindle oil and turbine oil; and fatty oils such as corn oil, soybean oil, olive oil, rapeseed oil, cotton seed oil, sardine oil, herring oil, and whale oil.

"Other" miscellaneous organic solvents can also be used, such as acetonitrile, nitromethane, dimethylformamide, propylene oxide, trioctyl phosphate, butyrolactone, furfural, pine oil, turpentine, and m-creosol.

Solvents may also include volatile flavoring agents such as oil of wintergreen; peppermint oil; spearmint oil; menthol; vanilla; cinnamon oil; clove oil; bay oil; anise oil; *eucalyptus* oil; thyme oil; cedar leaf oil; oil of nutmeg; oil of sage; *cassia* oil; cocoa; licorice; high fructose corn syrup; citrus oils such as lemon, orange, lime, and grapefruit; fruit essences such as apple, pear, peach, grape, strawberry, raspberry, cherry, plum, pineapple, and apricot; and other useful flavoring agents including aldehydes and esters such as cinnamyl acetate, cinnamaldehyde, eugenyl formate, p-methylanisole, acetaldehyde, benzaldehyde, anisic aldehyde, citral, neral, decanal, vanillin, tolyl aldehyde, 2,6-dimethyloctanal, and 2-ethyl butyraldehyde.

Moreover, solvents may include volatile fragrances such as natural products and perfume oils. Some representative natural products and perfume oils are ambergris, benzoin, civet, clove, leaf oil, jasmine, mate, mimosa, musk, myrrh, orris, sandalwood oil, and vetivert oil; aroma chemicals such as amyl salicylate, amyl cinnamic aldehyde, benzyl acetate, citronellol, coumarin, geraniol, isobornyl acetate, ambrette, and terpinyl acetate; and the various classic family perfume oils such as the floral bouquet family, the oriental family, the chypre family, the woody family, the citrus family, the canoe family, the leather family, the spice family, and the herbal family.

EXAMPLES

Example 1

20 g of aminoethylaminoisobutylsiloxane of about 400 dp and 2 mole % of amine was emulsified to a 100 gram emulsion. After formation of the emulsion, 100 g of the emulsion was combined with 0.24 gram of maleic anhydride to form a second emulsion and form the cross-linked aminosiloxane polymer. The second emulsion was mixed at room temperature for 20 min and then at 50° C. for 12 hours. A polymer internal phase was harvested by breaking the second emulsion with methanol and hexane. Results of temperature sweep experiments (depicted in FIG. 1) provide evidence for cross linking through comparison of the storage modulus (G') and loss modulus (G") where the G' is higher than G" for a crosslinked aminosiloxane polymer. The viscosity of the cross-linked aminosiloxane polymer increased from about 2500 cP to 1.7 E6 cP as measured by the Ares® controlled stress-rheometer.

Example 2

Figure 2:
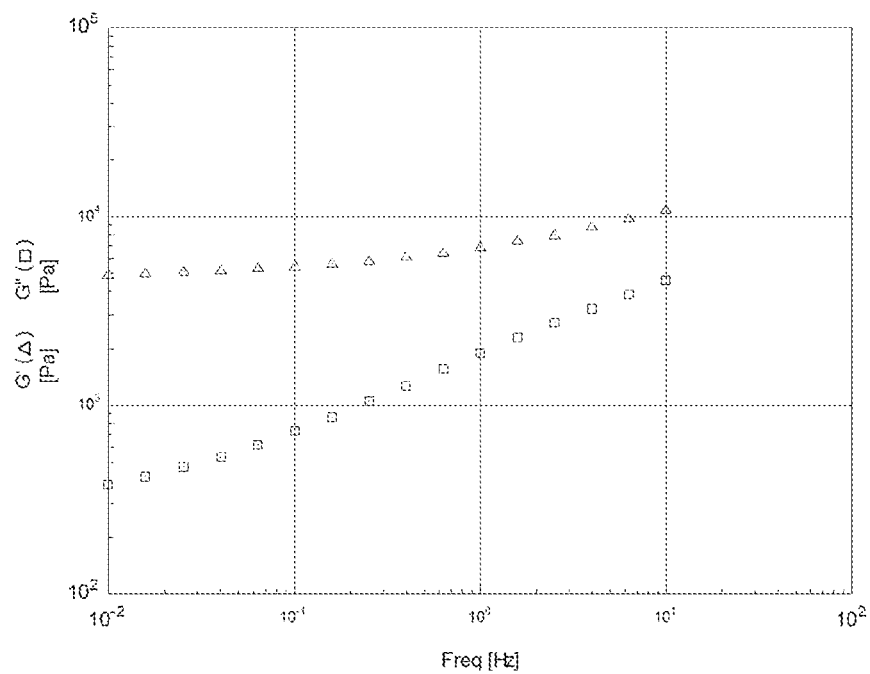
FIG. 2 is a plot of frequency modulation as related to Example 2.

20 g of aminopropylsiloxane of about 300 dp and 2 mole % of amine was emulsified to a 100 gram emulsion. After formation of the emulsion, 100 g of the emulsion was combined with 0.123 gram of maleic anhydride to form a second emulsion and form the cross-linked aminosiloxane polymer. The second emulsion was mixed at room temperature for 20 min and then at 50° C. for 12 hours. A polymer internal phase was harvested by breaking the second emulsion with methanol and hexane. Results of temperature sweep experiments (depicted in FIG. 2) provide evidence for cross linking through comparison of the storage modulus (G') and loss modulus (G") where the G' is higher than G" for a crosslinked aminosiloxane polymer. The viscosity of the cross-linked aminosiloxane polymer increased starting at about 1500 cP as measured by the Ares® controlled stress rheometer.

Example 3: Leave-in Conditioner

To form a single phase leave-in-conditioner, the following components are added to a vessel, in order, and mixed for 10 minutes.

| Ingredient - Single Phase Conditioner | Wt. % | Trade Name/Supplier |
|---|---|---|
| Water | q.s. to 100 | — |
| Panthenol | 1 | — |
| Glycerin | 3 | Glycerin USP/Fisher Scientific |
| O/W Emulsion of the Cross-Linked Aminosiloxane Polymer | 2.0 of Polymer | — |
| Aqua and Sodium Benzoate and Sodium Sorbate | 0.5 | Euxyl ® K712/Schulke & Mayr |

Example 4: Leave-in Conditioner

To form this Example, ingredient 1 is heated to 70° C. Subsequently, ingredient 2 is dispersed into ingredient 1 and mixed until homogeneous. Then ingredient 3 is added with gentle mixing.

In a separate vessel, phase B ingredients and combined and mixed. Phase B ingredients are then heated at 70° C. using a water bath. Subsequently, phase B ingredients are mixed together until all ingredients are completely dissolved. Then phase A is added to phase B in increments and stirred while keeping phase B ingredients warm enough to keep the wax melted. This combination is then stirred until homogeneous. Subsequently, the combination is cooled to room temperature while gently mixing. Phase C ingredients are then mixed in order listed below. Subsequently, the pH of the entire combination is adjusted to about 4 with citric acid solution.

| | Wt. % | Trade Name/Supplier |
|---|---|---|
| Phase A | | |
| Water | q.s. to 100 | |
| Hydroxyethylcellulose | 1.5 | Natrosol ® 250 HHR/Ashland Inc. |
| Glycerin | 5 | — |
| Phase B | | |
| Behentrimonium Methosulfate (and) Cetearyl Alcohol | 3 | Incroquat ™ Behenyl TMS/Croda |
| C10-40 | 2.5 | Cutissential ™ 18-MEA 40- |
| Isoalkylamidopropylethyl-dimonium Ethosulfate and Dipropylene Glycol | | NV-LQ-(MH)/Croda |
| Jojoba Oil | 1 | — |
| Cetyl Alcohol | 0.3 | Lanette ® 16/BASF Care Creations |
| Phase C | | |
| O/W Emulsion of the Cross-Linked Aminosiloxane Polymer | 2.0 silicone active | |
| Hydrolyzed Wheat Gluten | 0.1 | Gluadin ® W20/BASF Care Creations |
| Phenoxyethanol and Methylisothiazolinone | 0.1 | Neolone ™ PE/The Dow Chemical Company |
| Citric Acid (25% solution in water) | q.s. | — |

Example 5: Leave-in Conditioner

To form this Example, phase A ingredients are mixed until homogeneous. Then phase B ingredients are mixed until homogeneous. Phase B is then added to Phase A and the combination is mixed for an additional 10 minutes.

| | Wt. % | Trade Name/Supplier |
|---|---|---|
| Phase A | | |
| Lauryl PEG/PPG-18/18 Methicone | 2 | DOW CORNING ® 5200 FORMULATION AID |
| Jojoba Oil | 1.25 | |
| Isohexadecane | 11.25 | |
| Phase B | | |
| Glycerin | 3 | Glycerin USP/Fisher Scientific |
| O/W Emulsion of the Cross-Linked Aminosiloxane Polymer | 2.0 of Polymer | |
| Phenoxyethanol and Methylisothiazolinone | 0.5 | Neolone ™ PE/The Dow Chemical Company |
| Water | q.s. to 100 | |

Example 6: Rinse-Off Conditioner

To form this example, deionized water is added to the mixing vessel and heated to 75° C. With moderate agitation, the hydroxyethyl cellulose is dispersed until fully dissolved. Heat is decreased to 60° C. and cetearyl alcohol and PEG-100 stearate and glyceryl stearate is added. Heat is then decreased to 409 and the O/W Emulsion of the Cross-Linked Aminosiloxane Polymer is added to the base conditioner. The conditioner is mixed for 5-10 minutes and then the preservative is added. The water loss is compensated for and the formulation is mixed for an additional 5 minutes. The final pH of the conditioner formulation is approximately 6-7.

| Ingredient | Weight % | Trade Name Supplier |
|---|---|---|
| Deionized Water | q.s. to 100 | |
| Tetrasodium EDTA | 0.2 | Versene 220/The Dow Chemical Company |
| Hydroxyethylcellulose | 1.5 | Natrosol ® 250 HHR/Ashland Inc. |

| Ingredient | Weight % | Trade Name Supplier |
|---|---|---|
| Cetearyl Alcohol | 1.0 | Crodocol ® CS-50/Croda Inc. |
| PEG-100 Stearate & Glyceryl Stearate | 1.0 | Arlacel ™ 165/Croda Inc. |
| O/W Emulsion of the Cross-Linked Aminosiloxane Polymer | 2.0 of Polymer | |
| Phenoxyethanol and Methylisothiazolinone | 0.2 | Neolone ™ PE/The Dow Chemical Company |

Example 7: Conditioning Shampoo

To form this Example, deionized water is added to the mixing vessel. With moderate agitation, the polyquaternium-10 is dispersed until fully dissolved. This is then heated to 75° and the PEG-150 pentaerythrityl tetrastearate is added with continual mixing. Heat is decreased to 40° C. and sodium lauryl ether sulfate, cocamide DEA cocamidopropyl betaine are added in that order. When completely incorporated, the O/W Emulsion of the Cross-Linked Aminosiloxane Polymer is added to the base shampoo. The shampoo is mixed for 5-10 minutes and then preservative is added. The water loss is compensated for and the formulation is mixed for an additional 5 minutes. The final pH of the shampoo formulation is approximately 5.5-6.0.

| Ingredient | Weight % | Trade Name/Supplier |
|---|---|---|
| Water | q.s. to 100 | |
| Sodium Laureth Sulfate | 30 | Standapol ES-3 ®/BASF Care Creations |
| Cocamide DEA | 3.0 | Monamid 705 ®/Croda Inc. |
| Cocamidopropyl Betaine | 7.0 | Monateric CAB-LC ®/Croda Inc. |
| Polyquaternium-10 | 0.3 | UCARE ™ Polymer JR-30M/Dow Chemical Co. |
| PEG-150 Pentaerythrityl Tetrastearate | 1.5 | Crothix ®/Croda Inc. |
| O/W Emulsion of the Cross-Linked Aminosiloxane Polymer | 2.0 of Polymer | |
| Phenoxyethanol and Methylisothiazolinone | 0.2 | Neolone ™ PE/The Dow Chemical Company |

Hair tresses treated with the aforementioned examples demonstrate frizz control, curl retention, styling, alignment, straightening, shape, color protection, and overall conditioning benefits including improved combing and sensory feel attributes.

In various non-limiting embodiments, this disclosure includes one or more emulsions, compounds, reactants, method steps, or any other portion of the disclosure of concurrently filed U.S. Provisional Patent Application No. 62/001,427, now PCT/US15/031768, which is expressly incorporated herein in its entirety in these non-limiting embodiments.

One or more of the values described above may vary by ±5%, ±10%, ±15%, ±20%, ±25%, etc. so long as the variance remains within the scope of the disclosure. Unexpected results may be obtained from each member of a Markush group independent from all other members. Each member may be relied upon individually and or in combination and provides adequate support for specific embodiments within the scope of the appended claims. The subject matter of all combinations of independent and dependent claims, both singly and multiply dependent, is herein expressly contemplated. It is contemplated that any and all values or ranges of values between those described above may also be utilized. Moreover, all combinations of all chemistries, compounds, and concepts described above, and all values of subscripts and superscripts described above, are expressly contemplated in various non-limiting embodiments. The disclosure is illustrative including words of description rather than of limitation. Many modifications and variations of the present disclosure are possible in light of the above teachings, and the disclosure may be practiced otherwise than as specifically described herein.

EMBODIMENTS

Embodiment 1

An emulsion comprising:
A. a liquid continuous phase; and
B. a dispersed phase comprising a cross-linked aminosiloxane polymer comprising a first siloxane backbone, a second siloxane backbone, and at least one intramolecular structure cross-linking a silicon atom of said first siloxane backbone and a silicon atom of said second siloxane backbone, wherein said intramolecular structure has the chemical structure:

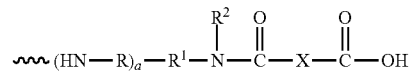

wherein X is chosen from the following groups;

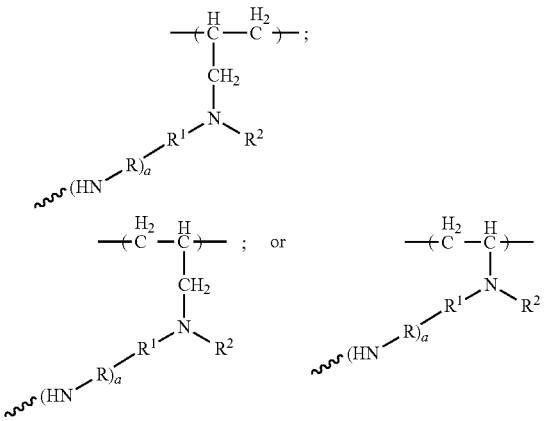

wherein each R is independently a $C_1$-$C_{10}$ hydrocarbon group;
wherein each $R^1$ is independently a $C_1$-$C_{10}$ hydrocarbon group;
wherein each $R^2$ is independently a hydrogen atom, OH, a $C_1$-$C_{12}$ hydrocarbon group, a phenyl group, R'(OR")$_m$ wherein m is 1 to 3; or R'OH, wherein each of R' and R" is independently an alkyl group; and
wherein a is 0 or 1.

Embodiment 2

The emulsion of embodiment 1 wherein said cross-linked aminosiloxane polymer has the chemical structure:

41

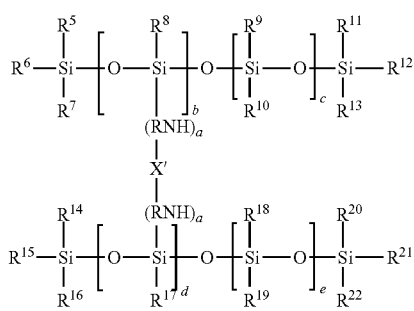

wherein X' is chosen from the following groups;

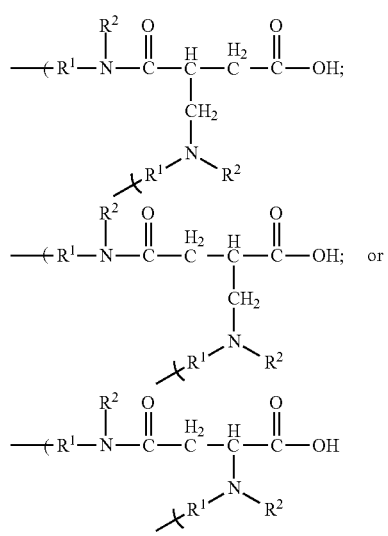

wherein each R is independently a $C_1$-$C_{10}$ hydrocarbon group;

wherein each $R^1$ is independently a $C_1$-$C_{10}$ hydrocarbon group;

wherein each $R^2$ is independently a hydrogen atom, OH, a $C_1$-$C_{12}$ hydrocarbon group, a phenyl group, R'(OR")$_m$ wherein m is 1 to 3; or R'OH, wherein each of R' and R" is independently an alkyl group;

wherein each of $R^5$-$R^{22}$ is independently a hydrogen atom, a $C_1$-$C_{12}$ hydrocarbon group, a $C_2$-$C_{12}$ akenyl group, a $C_6$-$C_{12}$ aromatic group, R'(OR")$_m$ or a polyalkyleneoxy group, wherein each of R' and R" is independently an alkyl group and m is 1 to 3;

wherein each of b and d is independently from 1 to 100;
wherein each of c and e is independently from 1 to 3,000; and
wherein a is 0 or 1.

Embodiment 3

The emulsion of Embodiment 1 or 2 wherein at least one $R^1$ is independently a $C_1$-$C_6$ hydrocarbon group.

Embodiment 4

The emulsion of any one of Embodiment 1-3 wherein at least one $R^2$ is a hydrogen atom.

42

Embodiment 5

The emulsion of any one of Embodiments 1-3 wherein at least one $R^2$ is OH.

Embodiment 6

The emulsion of any one of Embodiments 1-3 wherein at least one $R^2$ is a $C_1$-$C_{12}$ hydrocarbon group.

Embodiment 7

The emulsion of any one of Embodiments 1-3 wherein at least one $R^2$ is a phenyl group.

Embodiment 8

The emulsion of any one of Embodiments 1-3 wherein at least one $R^2$ is R'(OR")$_m$ wherein m is 1 to 3 and wherein each of R' and R" is independently an alkyl group.

Embodiment 9

The emulsion of any one of Embodiments 1-3 wherein at least one $R^2$ is R'OH, wherein R' is an alkyl group.

Embodiment 10

The emulsion of Embodiment 1 wherein said first siloxane backbone has the chemical structure:

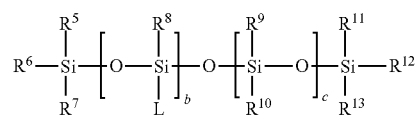

wherein each of $R^5$-$R^{13}$ is independently a hydrogen atom, a $C_1$-$C_{12}$ hydrocarbon group, a $C_2$-$C_{12}$ akenyl group, a $C_6$-$C_{12}$ aromatic group, R'(OR")$_m$ or a polyalkyleneoxy group, wherein each of R' and R" is independently an alkyl group and m is 1 to 3;

wherein b is from 1 to 100 and c is from 1 to 3,000; and
wherein L is said intramolecular structure.

Embodiment 11

The emulsion of Embodiment 1 or 10 wherein said second siloxane backbone has the chemical structure:

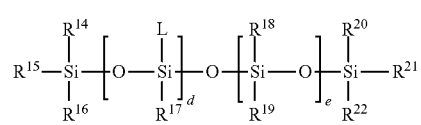

wherein each of $R^{14}$-$R^{22}$ is independently a hydrogen atom, a $C_1$-$C_{12}$ hydrocarbon group, a $C_2$-$C_{12}$ akenyl group, a $C_6$-$C_{12}$ aromatic group, R'(OR")$_m$ or a polyalkyleneoxy group, wherein each of R' and R" is independently an alkyl group and m is 1 to 3;

wherein d is from 1 to 100 and e is from 1 to 3,000; and wherein L is said intramolecular structure.

Embodiment 12

The emulsion of Embodiment 10 or 11 wherein each of $R^5$-$R^{22}$ is a hydrogen atom.

Embodiment 13

The emulsion of Embodiment 10 or 11 wherein at least one of $R^5$-$R^{22}$ is a hydrogen atom.

Embodiment 14

The emulsion of Embodiment 10 or 11 wherein each of $R^5$-$R^{22}$ is a $C_1$-$C_{12}$ hydrocarbon group.

Embodiment 15

The emulsion of Embodiment 10 or 11 wherein at least one of $R^5$-$R^{22}$ is a $C_1$-$C_{12}$ hydrocarbon group.

Embodiment 16

The emulsion of Embodiment 10 or 11 wherein at least one of $R^5$-$R^{22}$ is a phenyl group.

Embodiment 17

The emulsion of Embodiment 10 or 11 wherein at least one of $R^5$-$R^{22}$ is $R'(OR")_m$ wherein m is 1 to 3 and wherein each of R' and R" is independently an alkyl group.

Embodiment 18

The emulsion of Embodiment 10 or 11 wherein at least one of $R^5$-$R^{22}$ is R'OH, wherein R' is an alkyl group.

Embodiment 19

The emulsion of Embodiment 10 or 11 wherein at least one of $R^5$-$R^{22}$ is a methyl group.

Embodiment 20

The emulsion of any one of Embodiments 10-19 wherein at least one $R^1$ is independently a $C_1$-$C_6$ hydrocarbon group.

Embodiment 21

The emulsion of any one of Embodiments 10-20 wherein at least one $R^2$ is a hydrogen atom.

Embodiment 22

The emulsion of any one of Embodiments 10-20 wherein at least one $R^2$ is a $C_1$-$C_{12}$ hydrocarbon group.

Embodiment 23

The emulsion of any one of Embodiments 10-20 wherein at least one $R^2$ is OH.

Embodiment 24

The emulsion of any one of Embodiments 10-20 wherein at least one $R^2$ is a phenyl group.

Embodiment 25

The emulsion of any one of Embodiments 10-20 wherein at least one $R^2$ is $R'(OR")_m$ wherein m is 1 to 3 and wherein each of R' and R" is independently an alkyl group.

Embodiment 26

The emulsion of any one of Embodiments 10-20 wherein at least one $R^2$ is R'OH, wherein R' is an alkyl group.

Embodiment 27

The emulsion of Embodiment 1 wherein said cross-linked aminosiloxane polymer comprises the reaction product of a polyorganosiloxane having an amino group and a polyorganosiloxane that has an α,β-unsaturated carboxy acid amide group.

Embodiment 28

The emulsion of Embodiment 27 wherein said polyorganosiloxane having said amino group has the chemical formula:

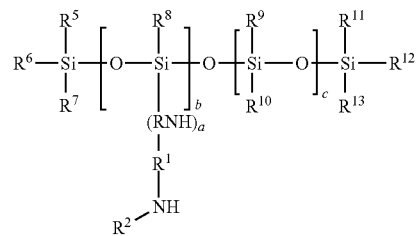

wherein R is independently a $C_1$-$C_{10}$ hydrocarbon group;
wherein $R^1$ is independently a $C_1$-$C_{10}$ hydrocarbon group;
wherein each $R^2$ is independently a hydrogen atom, OH, a $C_1$-$C_{12}$ hydrocarbon group, a phenyl group, $R'(OR")_m$ wherein m is 1 to 3; or R'OH, wherein each of R' and R" is independently an alkyl group;
wherein each of $R^5$-$R^{13}$ is independently a hydrogen atom, a $C_1$-$C_{12}$ hydrocarbon group, a $C_2$-$C_{12}$ akenyl group, a $C_6$-$C_{12}$ aromatic group, $R'(OR")_m$ or a polyalkyleneoxy group, wherein each of R' and R" is independently an alkyl group and m is 1 to 3;
wherein b is from 1 to 100;
wherein c is from 1 to 3,000; and
wherein a is 0 or 1.

Embodiment 29

The emulsion of Embodiment 27 or 28 wherein said polyorganosiloxane that has said α,β-unsaturated carboxy acid amide group has one of the following chemical formulas:

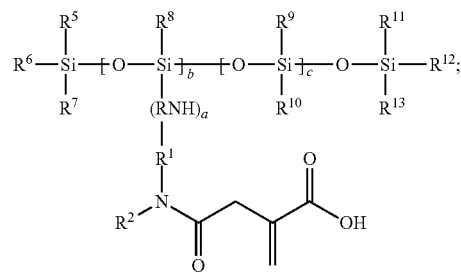

-continued

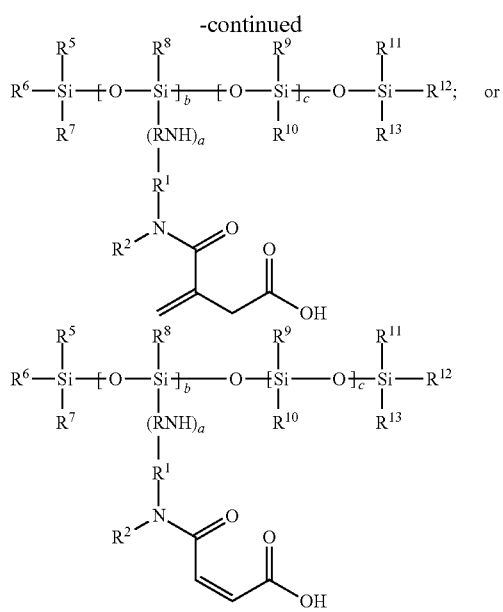

wherein R is independently a $C_1$-$C_{10}$ hydrocarbon group;
wherein $R^1$ is independently a $C_1$-$C_{10}$ hydrocarbon group;
wherein each $R^2$ is independently a hydrogen atom, OH, a $C_1$-$C_{12}$ hydrocarbon group, a phenyl group, $R'(OR")_m$ wherein m is 1 to 3; or R'OH, wherein each of R' and R" is independently an alkyl group;
wherein each of $R^5$-$R^{13}$ is independently a hydrogen atom, a $C_1$-$C_{12}$ hydrocarbon group, a $C_2$-$C_{12}$ akenyl group, a $C_6$-$C_{12}$ aromatic group, $R'(OR")_m$ or a polyalkyleneoxy group, wherein each of R' and R" is independently an alkyl group and m is 1 to 3;
wherein b is from 1 to 100;
wherein c is from 1 to 3,000; and
wherein a is 0 or 1.

Embodiment 30

The emulsion of Embodiment 29 wherein said polyorganosiloxane that has said α,β-unsaturated carboxy acid amide group is the reaction product of a second polyorganosiloxane and maleic anhydride and/or itaconic anhydride, wherein said second polyorganosiloxane has an amino group.

Embodiment 31

The emulsion of Embodiment 30 wherein said maleic anhydride and/or said itaconic anhydride reacts in an amount of from 0.01 to 0.33 moles per 1 mole of said amino group of said second organopolysiloxane.

Embodiment 32

The emulsion of Embodiment 30 or 31 wherein said polyorganosiloxane and said second polyorganosiloxane are the same.

Embodiment 33

The emulsion of Embodiment 30 or 31 wherein said polyorganosiloxane and said second polyorganosiloxane are different.

Embodiment 34

The emulsion of any preceding Embodiments wherein a is 1.

Embodiment 35

The emulsion of one of Embodiments 1-33 wherein a is 0.

Embodiment 36

The emulsion of any one of Embodiments 1-33 wherein R is independently a $C_1$-$C_6$ hydrocarbon group and a is 1.

Embodiment 37

The emulsion of any preceding Embodiments wherein said cross-linked aminosiloxane polymer of said dispersed phase is a gel.

Embodiment 38

The emulsion of any preceding Embodiments wherein said cross-linked aminosiloxane polymer of said dispersed phase is a liquid.

Embodiment 39

The emulsion of any preceding Embodiments wherein said cross-linked aminosiloxane polymer is present as particles dispersed in said continuous phase and said dispersed particles have a size of less than 15 μm.

Embodiment 40

The emulsion of any preceding Embodiments having a total viscosity of from 10 to 30,000 cps at 25° C.

Embodiment 41

The emulsion of any preceding Embodiments wherein said cross-linked aminosiloxane polymer is present in said emulsion in an amount of from 10 to 90 parts by weight per 100 parts by weight of said emulsion.

Embodiment 42

The emulsion of any preceding Embodiments further comprising a polydialkylsiloxane having a $M_w$ of up to 1,000,000 g/mol, wherein a ratio of said polydialkylsiloxane to said aminosiloxane polymer is from 0.1 to 100.

Embodiment 43

A water based composition comprising the emulsion set forth in any preceding Embodiments and chosen from cosmetic compositions, fabric treating compositions, hair care compositions, fiber care compositions, and combinations thereof.

Embodiment 44

A film formed from the emulsion of any one of Embodiments 1-42.

Embodiment 45

Use of the emulsion any one of Embodiments 1-42 as a cosmetic ingredient.

Embodiment 46

Use of the emulsion of any one of Embodiments 1-42 as a fabric treating agent.

Embodiment 47

Use of the emulsion of any one of Embodiments 1-42 as a fiber treating agent.

Embodiment 48

A cosmetic composition comprising the emulsion of any one of Embodiments 1-42.

Embodiment 49

A hair care composition comprising the emulsion of any one of Embodiments 1-42.

Embodiment 50

A fabric treating composition comprising the emulsion of any one of Embodiments 1-42.

Embodiment 51

A fiber treating composition comprising the emulsion of any one of Embodiments 1-42.

Embodiment 52

A method of forming a cross-linked aminosiloxane polymer in an emulsion, said method comprising the steps of:

I. providing a first emulsion comprising a first continuous phase and a first dispersed phase comprising a polyorganosiloxane having an amino group;

II. providing maleic anhydride and/or itaconic anhydride;

III. combining the maleic anhydride and/or itaconic anhydride and the first emulsion to form a second emulsion and the cross-linked aminosiloxane polymer in-situ in the second emulsion, wherein the second emulsion comprises a second continuous phase and a second dispersed phase comprising the cross-linked aminosiloxane polymer, wherein the cross-linked aminosiloxane polymer comprises a first siloxane backbone, a second siloxane backbone, and at least one intramolecular structure cross-linking a silicon atom of the first siloxane backbone and a silicon atom of the second siloxane backbone, wherein the intramolecular structure has the chemical structure:

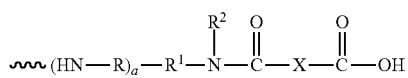

wherein X is chosen from the following groups;

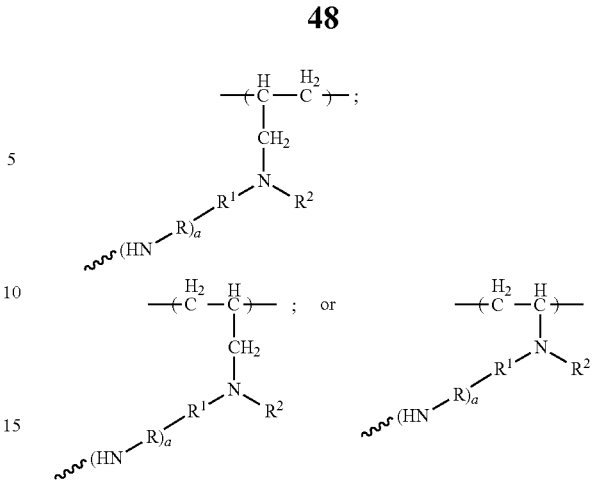

wherein each R is independently a $C_1$-$C_{10}$ hydrocarbon group;

wherein each $R^1$ is independently a $C_1$-$C_{10}$ hydrocarbon group;

wherein each $R^2$ is independently a hydrogen atom, OH, a $C_1$-$C_{12}$ hydrocarbon group, a phenyl group, $R'(OR'')_m$ wherein m is 1 to 3; or R'OH, wherein each of R' and R'' is independently an alkyl group; and wherein a is 0 or 1.

Embodiment 53

The method of Embodiment 52 further comprising the step of heating the second emulsion to a temperature of from 20° C. to 80° C.

Embodiment 54

The method of Embodiments 52 or 53 wherein the second emulsion is further defined as an oil-in-water emulsion.

Embodiment 55

The method of any one of Embodiments 52 to 54 wherein the step of providing the maleic anhydride and/or itaconic anhydride is further defined as providing 0.01 to 0.4 moles of maleic anhydride and/or itaconic anhydride per 1 mole of the amino group of the polyorganosiloxane having the amino group.

Embodiment 56

The method of any one of Embodiments 52 to 55 wherein the polyorganosiloxane having the amino group has the chemical formula:

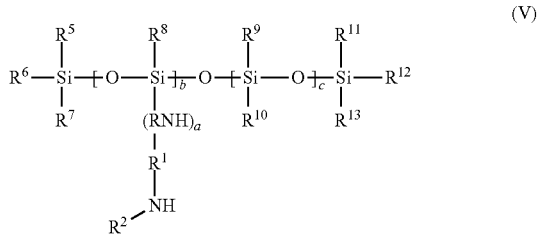

(V)

wherein R is independently a $C_1$-$C_{10}$ hydrocarbon group;

wherein $R^1$ is independently a $C_1$-$C_{10}$ hydrocarbon group;
wherein $R^2$ is independently a hydrogen atom, OH, a $C_1$-$C_{12}$ hydrocarbon group, a phenyl group, R'(OR")$_m$ wherein m is 1 to 3; or R'OH, wherein each of R' and R" is independently an alkyl group; and
wherein each of $R^5$-$R^{13}$ is independently a hydrogen atom, a $C_1$-$C_{12}$ hydrocarbon group, a $C_2$-$C_{12}$ akenyl group, a $C_6$-$C_{12}$ aromatic group, or a polyalkyleneoxy group;
wherein b is from 1 to 100;
wherein c is from 1 to 3,000; and
wherein a is 0 or 1.

Embodiment 57

The method of any one of Embodiments 52 to 56 wherein the maleic acid reacts with the polyorganosiloxane having the amino group to form a polyorganosiloxane in-situ in the second dispersed phase of the second emulsion, wherein the polyorganosiloxane has an α,β-unsaturated carboxy acid amide group.

Embodiment 58

The method of Embodiment 57 wherein the polyorganosiloxane that has the α,β-unsaturated carboxy acid amide group has the chemical formula:

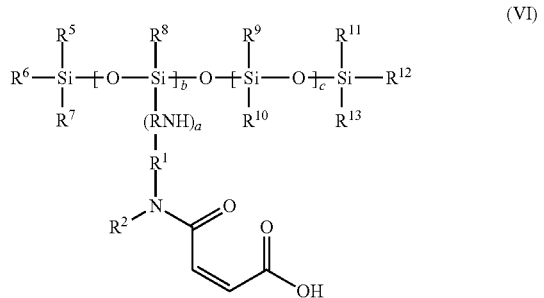

(VI)

wherein R is independently a $C_1$-$C_{10}$ hydrocarbon group;
wherein $R^1$ is independently a $C_1$-$C_{10}$ hydrocarbon group;
wherein $R^2$ is independently a hydrogen atom, OH, a $C_1$-$C_{12}$ hydrocarbon group, a phenyl group, R'(OR")$_m$ wherein m is 1 to 3; or R'OH, wherein each of R' and R" is independently an alkyl group; and
wherein each of $R^5$-$R^{13}$ is independently a hydrogen atom, a $C_1$-$C_{12}$ hydrocarbon group, a $C_2$-$C_{12}$ akenyl group, a $C_6$-$C_{12}$ aromatic group, or a polyalkyleneoxy group;
wherein b is from 1 to 100;
wherein c is from 1 to 3,000; and
wherein a is 0 or 1.

Embodiment 59

The method of Embodiment 57 or 58 wherein the polyorganosiloxane that has the α,β-unsaturated carboxy acid amide group reacts with the polyorganosiloxane having the amino group in-situ to form the cross-linked aminosiloxane polymer in the second dispersed phase of the second emulsion.

Embodiment 60

The method of any one of claims 52 to 59 wherein the aminosiloxane polymer has the chemical structure:

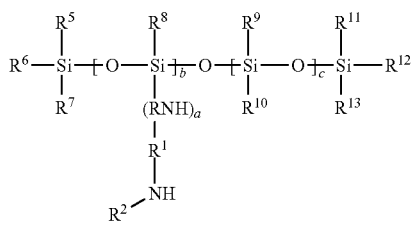

wherein R is independently a $C_1$-$C_{10}$ hydrocarbon group;
wherein $R^1$ is independently a $C_1$-$C_{10}$ hydrocarbon group;
wherein each $R^2$ is independently a hydrogen atom, OH, a $C_1$-$C_{12}$ hydrocarbon group, a phenyl group, R'(OR")$_m$ wherein m is 1 to 3; or R'OH, wherein each of R' and R" is independently an alkyl group;
wherein each of $R^5$-$R^{13}$ is independently a hydrogen atom, a $C_1$-$C_{12}$ hydrocarbon group, a $C_2$-$C_{12}$ akenyl group, a $C_6$-$C_{12}$ aromatic group, R'(OR")$_m$ or a polyalkyleneoxy group, wherein each of R' and R" is independently an alkyl group and m is 1 to 3;
wherein b is from 1 to 100;
wherein c is from 1 to 3,000; and
wherein a is 0 or 1.

Embodiment 61

The method of any one of Embodiments 52 to 60 wherein the polyorganosiloxane having the amino group is present in the first dispersed phase of the first emulsion in an amount of from 10 to 70 parts by weight per 100 parts by weight of the first emulsion.

Embodiment 62

The method of any one of Embodiments 52 to 61 wherein the polyorganosiloxane having the amino group is present in the second dispersed phase of the second emulsion in an amount of from 10 to 70 parts by weight per 100 parts by weight of the second emulsion.

Embodiment 63

The method of any one of Embodiments 52 to 62 wherein the maleic anhydride and/or itaconic anhydride is present in the second dispersed phase of the second emulsion in an amount of from 10 to 90 parts by weight per 100 parts by weight of the second emulsion.

Embodiment 64

The method of any one of Embodiments 52-63 wherein the first dispersed phase and/or the second dispersed phase further comprise a polydialkylsiloxane having a $M_w$ of up to 1,000,000 g/mol.

Embodiment 65

The method of Embodiment 64 wherein the second dispersed phase comprises the polydialkylsiloxane wherein a ratio of the polydialkylsiloxane to the aminosiloxane polymer is from 0.1 to 100.

What is claimed is:

1. An emulsion comprising:

A. a liquid continuous phase; and

B. a dispersed phase comprising a cross-linked aminosiloxane polymer comprising a first siloxane backbone, a second siloxane backbone, and at least one intramolecular structure cross-linking a silicon atom of said first siloxane backbone and a silicon atom of said second siloxane backbone, wherein said intramolecular structure has the chemical structure:

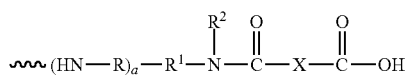

wherein X is chosen from the following groups;

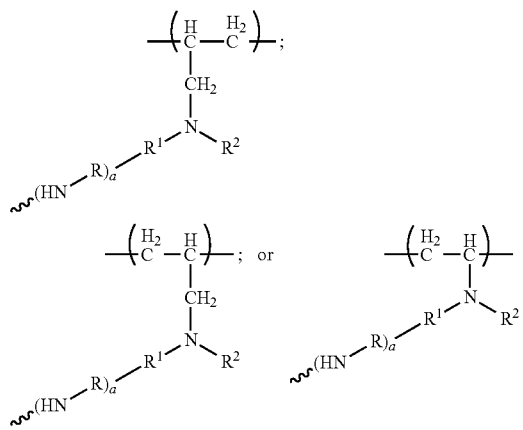

wherein each R is independently a $C_1$-$C_{10}$ hydrocarbon group;

wherein each $R^1$ is independently a $C_1$-$C_{10}$ hydrocarbon group;

wherein each $R^2$ is independently a hydrogen atom, OH, a $C_1$-$C_{12}$ hydrocarbon group, a phenyl group, $R'(OR'')_m$ wherein m is 1 to 3; or R'OH, wherein each of R' and R'' is independently an alkyl group; and wherein a is 0 or 1.

2. The emulsion of claim 1 wherein said cross-linked aminosiloxane polymer has the chemical structure:

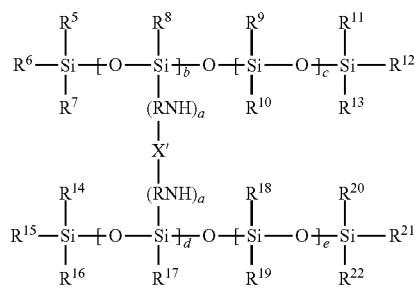

wherein X' is chosen from the following groups;

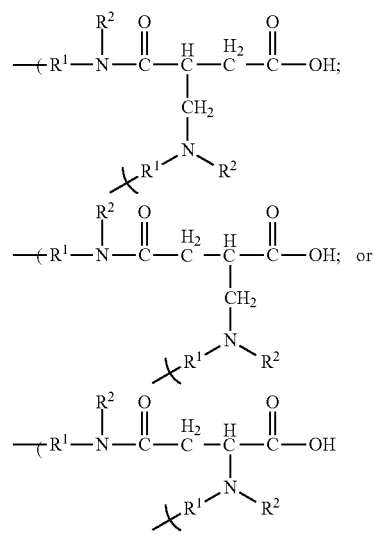

wherein each R is independently a $C_1$-$C_{10}$ hydrocarbon group;

wherein each $R^1$ is independently a $C_1$-$C_{10}$ hydrocarbon group;

wherein each $R^2$ is independently a hydrogen atom, OH, a $C_1$-$C_{12}$ hydrocarbon group, a phenyl group, $R'(OR'')_m$ wherein m is 1 to 3; or R'OH, wherein each of R' and R'' is independently an alkyl group;

wherein each of $R^5$-$R^{22}$ is independently a hydrogen atom, a $C_1$-$C_{12}$ hydrocarbon group, a $C_2$-$C_{12}$ alkenyl group, a $C_6$-$C_{12}$ aromatic group, $R'(OR'')_m$ or a polyalkyleneoxy group, wherein each of R' and R'' is independently an alkyl group and m is 1 to 3;

wherein each of b and d is independently from 1 to 100;

wherein each of c and e is independently from 1 to 3,000; and wherein a is 0 or 1.

3. The emulsion of claim 1 wherein said first siloxane backbone has the chemical structure:

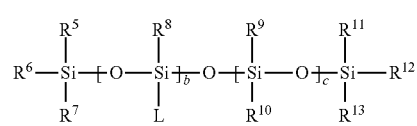

wherein each of $R^5$-$R^{13}$ is independently a hydrogen atom, a $C_1$-$C_{12}$ hydrocarbon group, a $C_2$-$C_{12}$ alkenyl group, a $C_6$-$C_{12}$ aromatic group, $R'(OR'')_m$ or a polyalkyleneoxy group, wherein each of R' and R'' is independently an alkyl group and m is 1 to 3;

wherein b is from 1 to 100 and c is from 1 to 3,000; and wherein L is said intramolecular structure.

4. The emulsion of claim 1 wherein said second siloxane backbone has the chemical structure:

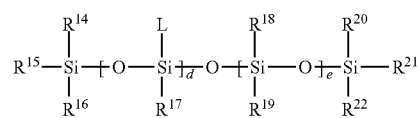

wherein each of $R^{14}$-$R^{22}$ is independently a hydrogen atom, a $C_1$-$C_{12}$ hydrocarbon group, a $C_2$-$C_{12}$ alkenyl group, a $C_6$-$C_{12}$ aromatic group, R'(OR")$_m$ or a polyalkyleneoxy group, wherein each of R' and R" is independently an alkyl group and m is 1 to 3;

wherein d is from 1 to 100 and e is from 1 to 3,000; and wherein L is said intramolecular structure.

5. The emulsion of claim 1 wherein said cross-linked aminosiloxane polymer comprises the reaction product of a polyorganosiloxane having an amino group and a polyorganosiloxane that has an α,β-unsaturated carboxy acid amide group.

6. The emulsion of claim 5 wherein said polyorganosiloxane having said amino group has the chemical formula:

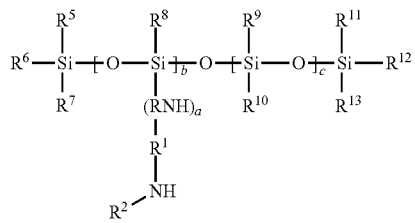

wherein R is independently a $C_1$-$C_{10}$ hydrocarbon group;
wherein $R^1$ is independently a $C_1$-$C_{10}$ hydrocarbon group;
wherein each $R^2$ is independently a hydrogen atom, OH, a $C_1$-$C_{12}$ hydrocarbon group, a phenyl group, R'(OR")$_m$ wherein m is 1 to 3; or R'OH, wherein each of R' and R" is independently an alkyl group;
wherein each of $R^5$-$R^{13}$ is independently a hydrogen atom, a $C_1$-$C_{12}$ hydrocarbon group, a $C_2$-$C_{12}$ alkenyl group, a $C_6$-$C_{12}$ aromatic group, R'(OR")$_m$ or a polyalkyleneoxy group, wherein each of R' and R" is independently an alkyl group and m is 1 to 3;
wherein b is from 1 to 100;
wherein c is from 1 to 3,000; and
wherein a is 0 or 1.

7. The emulsion of claim 5 wherein said polyorganosiloxane that has said α,β-unsaturated carboxy acid amide group has one of the following chemical formulas:

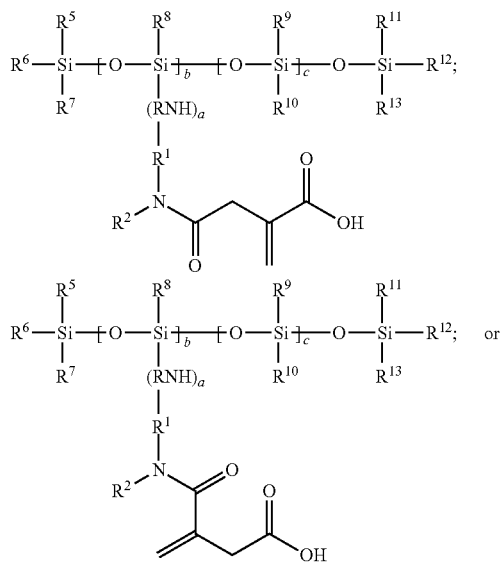

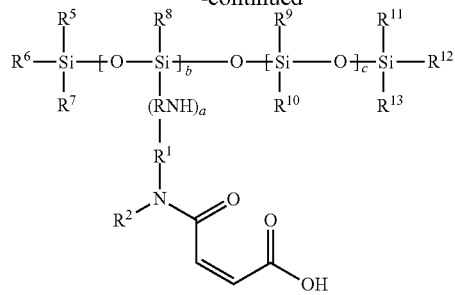

wherein R is independently a $C_1$-$C_{10}$ hydrocarbon group;
wherein $R^1$ is independently a $C_1$-$C_{10}$ hydrocarbon group;
wherein each $R^2$ is independently a hydrogen atom, OH, a $C_1$-$C_{12}$ hydrocarbon group, a phenyl group, R'(OR")$_m$ wherein m is 1 to 3; or R'OH, wherein each of R' and R" is independently an alkyl group;
wherein each of $R^5$-$R^{13}$ is independently a hydrogen atom, a $C_1$-$C_{12}$ hydrocarbon group, a $C_2$-$C_{12}$ alkenyl group, a $C_6$-$C_{12}$ aromatic group, R'(OR")$_m$ or a polyalkyleneoxy group, wherein each of R' and R" is independently an alkyl group and m is 1 to 3;
wherein b is from 1 to 100;
wherein c is from 1 to 3,000; and
wherein a is 0 or 1.

8. The emulsion of claim 7 wherein said polyorganosiloxane that has said α,β-unsaturated carboxy acid amide group is the reaction product of a second polyorganosiloxane and maleic anhydride and/or itaconic anhydride, wherein said second polyorganosiloxane has an amino group.

9. The emulsion of claim 8 wherein said maleic anhydride and/or said itaconic anhydride reacts in an amount of from 0.01 to 0.33 moles per 1 mole of said amino group of said second organopolysiloxane.

10. The emulsion of claim 8 wherein said polyorganosiloxane and said second polyorganosiloxane are the same or different.

11. The emulsion of claim 1 comprising one or more of limitations a) through f)
 a) wherein a is 1 or a is 0;
 b) wherein said cross-linked aminosiloxane polymer of said dispersed phase is a gel or liquid;
 c) wherein said cross-linked aminosiloxane polymer is present as particles dispersed in said continuous phase and said dispersed particles have a size of less than 15 μm;
 d) wherein the emulsion has a total viscosity of from 10 to 30,000 cps at 25° C.;
 e) wherein said cross-linked aminosiloxane polymer is present in said emulsion in an amount of from 10 to 90 parts by weight per 100 parts by weight of said emulsion;
 f) wherein the emulsion further comprises a polydialkylsiloxane having a $M_w$ of up to 1,000,000 g/mol, wherein a ratio of said polydialkylsiloxane to said aminosiloxane polymer is from 0.1 to 100.

12. A water based composition comprising the emulsion set forth in claim 1 and chosen from cosmetic compositions, fabric treating compositions, hair care compositions, fiber care compositions, and combinations thereof.

13. A film formed from the emulsion of claim 1.

14. A method of forming a cross-linked aminosiloxane polymer in an emulsion, said method comprising the steps of:

I. providing a first emulsion comprising a first continuous phase and a first dispersed phase comprising a polyorganosiloxane having an amino group;
II. providing maleic anhydride and/or itaconic anhydride;
III. combining the maleic anhydride and/or itaconic anhydride and the first emulsion to form a second emulsion and the cross-linked aminosiloxane polymer in-situ in the second emulsion,
wherein the second emulsion comprises a second continuous phase and a second dispersed phase comprising the cross-linked aminosiloxane polymer,
wherein the cross-linked aminosiloxane polymer comprises a first siloxane backbone, a second siloxane backbone, and at least one intramolecular structure cross-linking a silicon atom of the first siloxane backbone and a silicon atom of the second siloxane backbone, wherein the intramolecular structure has the chemical structure:

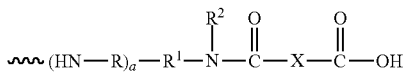

wherein X is chosen from the following groups;

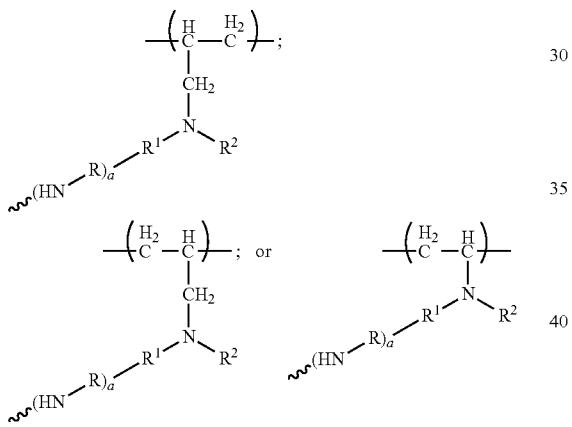

wherein each R is independently a $C_1$-$C_{10}$ hydrocarbon group;
wherein each $R^1$ is independently a $C_1$-$C_{10}$ hydrocarbon group;
wherein each $R^2$ is independently a hydrogen atom, OH, a $C_1$-$C_{12}$ hydrocarbon group, a phenyl group, R'(OR")$_m$ wherein m is 1 to 3; or R'OH, wherein each of R' and R" is independently an alkyl group; and
wherein a is 0 or 1.

15. The method of claim 14 comprising one or more of limitations g) through j)
g) further comprising the step of heating the second emulsion to a temperature of from 20° C. to 80° C.;
h) wherein the second emulsion is further defined as an oil-in-water emulsion;
i) wherein the step of providing the maleic anhydride and/or itaconic anhydride is further defined as providing 0.01 to 0.4 moles of maleic anhydride and/or itaconic anhydride per 1 mole of the amino group of the polyorganosiloxane having the amino group;
j) wherein the polyorganosiloxane having the amino group has the chemical formula:

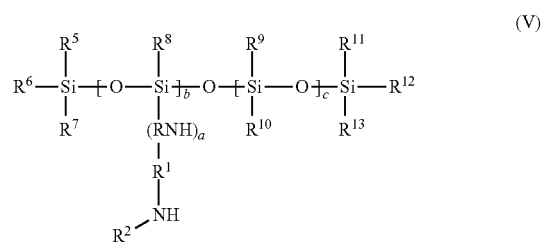

wherein R is independently a $C_1$-$C_{10}$ hydrocarbon group;
wherein $R^1$ is independently a $C_1$-$C_{10}$ hydrocarbon group;
wherein $R^2$ is independently a hydrogen atom, OH, a $C_1$-$C_{12}$ hydrocarbon group, a phenyl group, R'(OR")$_m$ wherein m is 1 to 3; or R'OH, wherein each of R' and R" is independently an alkyl group; and
wherein each of $R^5$-$R^{13}$ is independently a hydrogen atom, a $C_1$-$C_{12}$ hydrocarbon group, a $C_2$-$C_{12}$ alkenyl group, a $C_6$-$C_{12}$ aromatic group, or a polyalkyleneoxy group;
wherein b is from 1 to 100;
wherein c is from 1 to 3,000; and
wherein a is 0 or 1.

16. The method of claim 14 wherein the maleic acid reacts with the polyorganosiloxane having the amino group to form a polyorganosiloxane in-situ in the second dispersed phase of the second emulsion, wherein the polyorganosiloxane has an α,β-unsaturated carboxy acid amide group.

17. The method of claim 16 wherein the polyorganosiloxane that has the α,β-unsaturated carboxy acid amide group has the chemical formula:

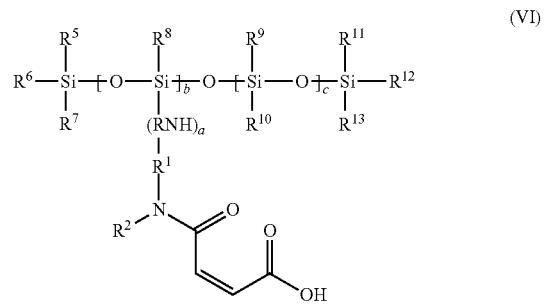

wherein R is independently a $C_1$-$C_{10}$ hydrocarbon group;
wherein $R^1$ is independently a $C_1$-$C_{10}$ hydrocarbon group;
wherein $R^2$ is independently a hydrogen atom, OH, a $C_1$-$C_{12}$ hydrocarbon group, a phenyl group, R'(OR")$_m$ wherein m is 1 to 3; or R'OH, wherein each of R' and R" is independently an alkyl group; and
wherein each of $R^5$-$R^{13}$ is independently a hydrogen atom, a $C_1$-$C_{12}$ hydrocarbon group, a $C_2$-$C_{12}$ alkenyl group, a $C_6$-$C_{12}$ aromatic group, or a polyalkyleneoxy group;
wherein b is from 1 to 100;
wherein c is from 1 to 3,000; and
wherein a is 0 or 1.

18. The method of claim 16 wherein the polyorganosiloxane that has the α,β-unsaturated carboxy acid amide group reacts with the polyorganosiloxane having the amino group in-situ to form the cross-linked aminosiloxane polymer in the second dispersed phase of the second emulsion.

19. The method of claim 14 wherein the aminosiloxane polymer has the chemical structure:

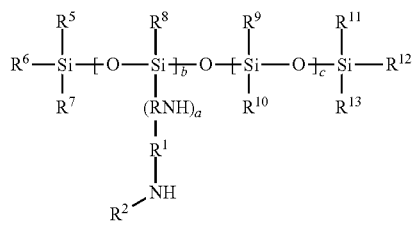

wherein R is independently a $C_1$-$C_{10}$ hydrocarbon group;
wherein $R^1$ is independently a $C_1$-$C_{10}$ hydrocarbon group;
wherein each $R^2$ is independently a hydrogen atom, OH, a $C_1$-$C_{12}$ hydrocarbon group, a phenyl group, $R'(OR")_m$ wherein m is 1 to 3; or R'OH, wherein each of R' and R" is independently an alkyl group;
wherein each of $R^5$-$R^{13}$ is independently a hydrogen atom, a $C_1$-$C_{12}$ hydrocarbon group, a $C_2$-$C_{12}$ alkenyl group, a $C_6$-$C_{12}$ aromatic group, $R'(OR")_m$ or a polyalkyleneoxy group, wherein each of R' and R" is independently an alkyl group and m is 1 to 3;
wherein b is from 1 to 100;
wherein c is from 1 to 3,000; and
wherein a is 0 or 1.

20. The method of claim 14, further comprising one or more of limitations k) through n):
  k) wherein the polyorganosiloxane having the amino group is present in the first dispersed phase of the first emulsion in an amount of from 10 to 70 parts by weight per 100 parts by weight of the first emulsion;
  l) wherein the maleic anhydride and/or itaconic anhydride is present in the second dispersed phase of the second emulsion in an amount of from 10 to 90 parts by weight per 100 parts by weight of the second emulsion;
  m) wherein the first dispersed phase and/or the second dispersed phase further comprise a polydialkylsiloxane having a $M_w$ of up to 1,000,000 g/mol;
  n) limitation m) wherein the second dispersed phase comprises the polydialkylsiloxane and wherein a ratio of the polydialkylsiloxane to the aminosiloxane polymer is from 0.1 to 100.

* * * * *